(12) United States Patent
Betz et al.

(10) Patent No.: US 11,643,420 B2
(45) Date of Patent: May 9, 2023

(54) BENZOXAZINONE COMPOUNDS AS KLK5/7 DUAL INHIBITORS

(71) Applicant: MOLECULAR SKIN THERAPEUTICS, INC., Palo Alto, CA (US)

(72) Inventors: Andreas Betz, Palo Alto, CA (US); Robert Zamboni, Palo Alto, CA (US)

(73) Assignee: MOLECULAR SKIN THERAPEUTICS, INC., Palo Alto, CA (US)

( * ) Notice: Subject to any disclaimer, the term of this patent is extended or adjusted under 35 U.S.C. 154(b) by 149 days.

(21) Appl. No.: 17/037,910

(22) Filed: Sep. 30, 2020

(65) Prior Publication Data

US 2021/0101911 A1     Apr. 8, 2021

Related U.S. Application Data

(60) Provisional application No. 62/909,006, filed on Oct. 1, 2019.

(51) Int. Cl.
| | | |
|---|---|---|
| *C07D 498/04* | (2006.01) | |
| *A61P 17/00* | (2006.01) | |
| *A61K 9/00* | (2006.01) | |

(52) U.S. Cl.
CPC .......... *C07D 498/04* (2013.01); *A61K 9/0014* (2013.01); *A61P 17/00* (2018.01)

(58) Field of Classification Search
None
See application file for complete search history.

(56) References Cited

U.S. PATENT DOCUMENTS

| 4,980,287 A | 12/1990 | Kokubo et al. |
| 2003/0187256 A1 | 10/2003 | Berrmany et al. |
| 2017/0002021 A1 | 1/2017 | Wagberg et al. |

FOREIGN PATENT DOCUMENTS

| WO | 2004/108139 A2 | 12/2004 | |
| WO | 2004/108139 A3 | 12/2004 | |
| WO | 2015/112081 A1 | 7/2015 | |
| WO | WO 2015/112081 | * 7/2015 | .......... C07D 265/20 |

OTHER PUBLICATIONS

Kalinska et al (Biochime 122:270-282, 2016) (Year: 2016).*
Di Paolo et al (Critical Reviews in Clinical Laboratory Sciences 581-16, 2021) (Year: 2021).*
Novartis Pharma AG (Clinical Trial Results Website, Feb. 13, 2015 (Year: 2015).*
International Search Report dated Jan. 22, 2021 corresponding to PCT/US2020/053369 filed Sep. 30, 2020; 14 pages.
Kantyka, Tomasz et al., "Inhibition of kallikrien-related peptidases by the serine protease inhibitor of Kazal-type 6," *Peptide* (2011; available online Mar. 23, 2011) 32:1187-1192.
PUBCHEM 2993515 deposited Jul. 29, 2005; pp. 1-6.

* cited by examiner

*Primary Examiner* — Craig D Ricci
(74) *Attorney, Agent, or Firm* — Mintz Levin Cohn Ferris Glovsky and Popeo PC

(57) ABSTRACT

The present invention provides compounds and pharmaceutical compositions including the compounds for the treatment of a skin disease associated with proteolytic activity of one or more KLK proteases, wherein the compounds are according to formula (I):

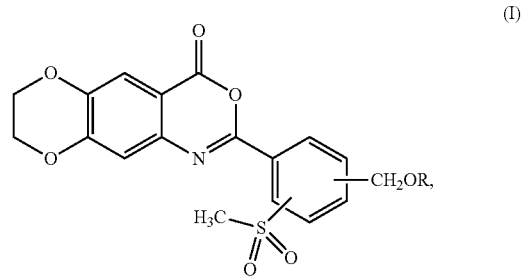

wherein R is as described herein.

14 Claims, 7 Drawing Sheets

Specification includes a Sequence Listing.

BENZOXAZINONE COMPOUNDS AS KLK5/7 DUAL INHIBITORS

CROSS-REFERENCES TO RELATED APPLICATIONS

This application claims priority to U.S. Provisional Application No. 62/909,006 filed Oct. 1, 2019, which is incorporated herein in its entirety for all purpose.

STATEMENT AS TO RIGHTS TO INVENTIONS MADE UNDER FEDERALLY SPONSORED RESEARCH AND DEVELOPMENT

Not Applicable

REFERENCE TO A "SEQUENCE LISTING," A TABLE, OR A COMPUTER PROGRAM LISTING APPENDIX SUBMITTED ON A COMPACT DISK REFERENCE TO A "SEQUENCE LISTING,"

The Sequence_Listing.txt, modified on Dec. 3, 2020 (4 KB in size), machine format IBM-PC, MS-Windows operating system, is hereby incorporated by reference in its entirety for all purposes.

BACKGROUND OF THE INVENTION

Genodermatoses are genetic diseases that are expressed as skin conditions. The diseases are usually detectable upon birth if not soon after. The type of disease depends on how the genes are affected but the resultant conditions can be serious, rare and severely affect the patient's life by leading to disabilities, a short life span, and the development of other chronic diseases and cancer. There are approximately 400 different kinds of genodermatoses with an incidence that can vary from between 1 in 6000 people to 1 in 500,000 people. The burden of the disease can be difficult for the patient and families who potentially have access to only a very limited range of expensive medicines to help in disease management. Genodermatoses can divide to single gene disorders (monogenic) where skin disorders are caused by an abnormality in a single gene and polygenic disorders where several gene mutations (defects) influence the type of disease that the patient experiences. The single gene disorders include acute intermittent porphyrin, epidermolysis bullosa, ichthyosis, fabry disease, anhidrotic ectodermal dysplasia, and incontinence pigmenti. Genetic diseases with ichthyosis include Netherton Syndrome.

Netherton Syndrome (NS) is a rare autosomal recessive genodermatosis characterized by congenital ichthyosiform erythroderma, an atopic diathesis, and a characteristic hair-shaft abnormality known as trichorrhexis invaginata. Netherton Syndrome is one of the most severe disorders of cornification. Infants typically present at birth with a generalized scaling erythroderma and have a high risk of life-threatening complications, such as hypernatremic dehydration, failure to thrive, and sepsis. In older children, a wide range of allergic manifestations may occur, including severe atopic dermatitis, asthma, hay fever, and markedly elevated serum levels of immunoglobulin E. In older children and adults the scaling may have a distinctive circular pattern (ichthyosis linearis circumflexa). But in infants and younger children, the skin is more commonly red and scaly all over, lacking the distinctive circular pattern. Hair shafts are fragile and break easily due to trichorrhexis invaginata, or "bamboo hair," resulting in short sparse hair. Another characteristic of Netherton Syndrome is a predisposition to allergies, asthma, and eczema. Adults and children with Netherton Syndrome are also predisposed viral skin infections with herpes and human papilloma virus, in addition to bacterial skin and systemic infections. Netherton Syndrome incidence is estimated at 1/200,000 births and prevalence is estimated at 1-9/1,000,000. Nevertheless, regional studies suggest prevalence may be higher due to diagnostic challenges during infancy and early childhood, including overlapping features with atopic dermatitis and other recessive ichthyoses. Currently, there is no specific therapy for NS but only palliative treatments for management of skin infections, reduction of itching and pain.

NS is caused by truncated loss-of-function mutations of the serine protease inhibitor Kazal-type 5 (SPINK5), a gene that encodes LEKTI (lymphoepithelial Kazal-type inhibitor). LEKTI loss-of-function results in unopposed protease activities and over digestion of epidermal structural and barrier proteins.

LETKI is an inhibitor specific for kallikrein (KLK) serine protease family members (KLK5, KLK7, and KLK14) (Chavanas et al., Nat Genet 2000, 25: 141-142). KLK5 is characterized as an initiator upstream of KLK7. According to the current state-of-hypothesis, pro-KLKs are synthesized and activated in the stratum granulosum and active KLK enzymes are rapidly complexed with LEKTI, thus preventing premature degradation of desmosomes at the stratum corneum/stratum granulosum interface (Borgono et al, *J Biol Chem* 2007, 282:3640-3652; Deraison et al, *Mol Biol Cell* 2007, 18:3607-3619; Ovaere et al, *Trends Biochem Sci* 2009, 34:453-463). KLK-LEKTI complexes diffuse to the outer stratum corneum where the acidic microenvironment of stratum corneum causes the release of active KLKs from LEKTI. Subsequently, the active KLKs cleave corneodesmosomal proteins in the most superficial layers of the stratum corneum. This ensures the finely balanced regulation of the desquamation process (Ovaere et al., *Trends Biochem Sci* 2009, 34:453-463).

Spink5$^{-/-}$ mice recapitulate NS disease (Descargues et al, *Nat Genet* 2005, 37:56-65; Hewett et al, *Hum Mol Genet* 2005, 14:335-346; Yang et al, *Genes Dev* 2004, 18:2354-2358). A key finding is that, similarly to what has been observed in subjects with NS, Spink5$^{-/-}$ mice epidermis displays unopposed KLK5 and KLK7 protease activities (Descargues et al, *Nat Genet* 2005, 37:56-65).

Conversely, deletion of KLK5 rescues neonatal lethality in Spink5$^{-/-}$ newborn mice, and reverses cutaneous hallmarks of NS, including skin barrier defect, disordered epidermal structure, and skin inflammation (Furio et al., *PLoS Genet* 2015, September; 11(9): e1005389). Notably, KLK5 loss results in reduced epidermal proteolytic activity, particularly KLK7 and KLK14. Subsequently, it restores structural integrity of desmosomes and corneodesmosomes and normal epidermal differentiation as well as normalized expressions of IL-1β, IL-17A, and TSLP (thymic stromal lymphopoietin).

In addition to animal models, organotypic 3D cultures are generated with normal human keratinocytes transfected with SPINKS-targeted small interfering RNA (siRNA) and fibroblast-populated collagen gels and the epidermal defects are observed in these culture models (Wang et al., *Exp Dermatol* 2014, July; 23(7):524-6). Gene silencing of KLK5 or KLK7 markedly ameliorates the epidermal architecture compromised by reduced SPINK5 expression. Together, these studies confirm a major role of KLK5 and its upstream and downstream regulators in NS.

KLK7 is expressed by keratinocytes in the stratum granulosum and secreted to the stratum corneum (i.e. the outermost layer of the skin) extracellular space as a zymogen subsequently activated by KLK5. Once activated, KLK7 plays a central role in the desquamation process of the skin. The proteolytic events of KLK7 are essential for the desquamation process and for the controlled regeneration of the skin. A tight balance between production of new corneocytes and desquamation is essential for the maintenance of skin homeostasis. In contrast, a misbalance between these two processes results in an impaired skin function and ultimately in dermatological diseases such as Netherton Syndrome. In normal conditions, this balance is maintained by the expression of endogenous protein inhibitors (LEKTI) of KLK7 counteracting its proteolytic activity. In skin disorders, KLK7 overexpression and/or increased activity result in over-desquamation. The involvement of KLK7 in the development of skin disorders is further supported by genetic association in both animal models and humans. It has been shown that transgenic mice overexpressing human KLK7 develop skin features similar to those seen in chronic atopic dermatitis patients, who share certain features in common with Netherton Syndrome patients.

In view of roles of KLK5 and KLK7 in regulating the desquamation process, and taken together with the reported results of a full phenotypic rescue from a combination Spink5$^{-/-}$/Klk5$^{-/-}$/Klk7$^{-/-}$ knockout mouse model (Kasparek et al., *PLoS Genet* 2017, January; 13(1): e1006566), therefore potent and selective dual KLK5/KLK7 inhibitors are needed for the treatment of genodermatosis, for example, Netherton Syndrome by modulating the proteolytic activity of these proteases.

BRIEF SUMMARY OF THE INVENTION

In one aspect, the present invention provides a compound represented by formula (I):

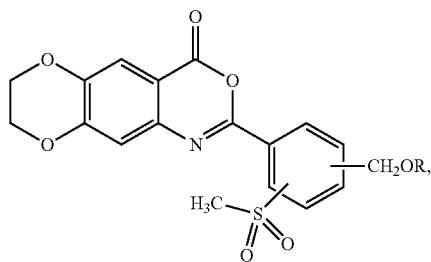

(I)

or a pharmaceutically acceptable complex thereof; wherein R is H or a member selected from the group consisting of —R$^1$ and —C(O)R$^{1a}$, wherein R$^1$ is C$_{1-12}$ alkyl, and R$^{1a}$ is H or C$_{1-12}$ alkyl.

In a second aspect, the present invention provides a pharmaceutical composition including the compound of formula (I) or a pharmaceutically acceptable complex thereof and a pharmaceutically acceptable carrier.

In a third aspect, the present invention provides a method for treating a skin disease associated with proteolytic activity of one or more KLK proteases in a subject in need thereof. The method includes administering the subject an effective amount of the compound of formula (I) or a pharmaceutically acceptable complex thereof, or the pharmaceutical composition including the compound of formula (I) or a pharmaceutically acceptable complex thereof.

In a fourth aspect, the present invention provides an in vitro assay for determining proteolytic activity of one or more KLK proteases in a skin. The method includes 1) preparing a skin extract; 2) exposing a substrate and the compound of formula (I) or a pharmaceutically acceptable complex thereof to the skin extract; and 3) determining a rate of proteolytic cleavage of the substrate.

BRIEF DESCRIPTION OF THE DRAWINGS

FIG. 4A: Control;
FIG. 4B: Compound 14;
FIG. 4C: Compound 1.001;
and FIG. 4D: Compound 1.002. NSK refers to extract from skin freshly prepared; and OSK refers to extract from skin post freeze thaw.

DETAILED DESCRIPTION OF THE INVENTION

I. General

Figure 1:
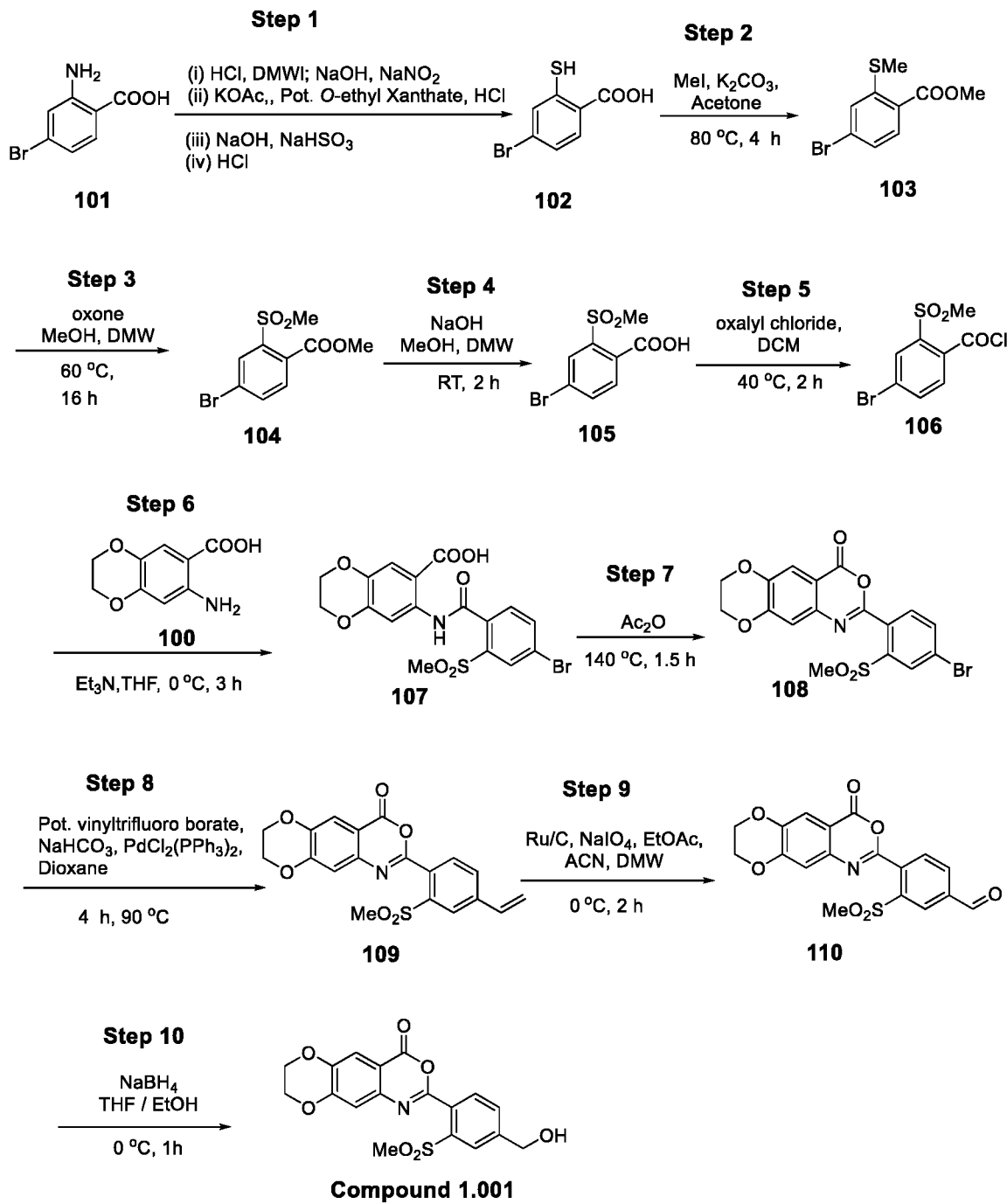
FIG. 1 shows a scheme for preparing Compound 1.001.

The present invention provides compounds of formula (I) and pharmaceutical compositions including the compounds of formula (I) for the treatment of a skin disease associated with proteolytic activity of one or more KLK proteases. In particular, pharmaceutical compositions can be topical formulations including the compounds of formula (I) for topical use in treating genodermatoses. The present invention also provides methods of treating a skin disease associated with proteolytic activity of one or more KLK proteases by administering the compounds of formula (I) or pharmaceutical compositions thereof. In particular the compounds of formula (I) or pharmaceutical compositions thereof can be administered topically. Specifically, the skin disease is a genodermatosis such as Netherton Syndrome.

II. Definitions

The abbreviations used herein have their conventional meaning within the chemical and biological arts.

"Alkyl" refers to a straight or branched, saturated, aliphatic radical having the number of carbon atoms indicated (i.e., C$_{1-12}$ means one to twelve carbons). Alkyl can include any number of carbons, such as C$_{1-2}$, C$_{1-3}$, C$_{1-4}$, C$_{1-5}$, C$_{1-6}$, C$_{1-7}$, C$_{1-8}$, C$_{1-9}$, C$_{1-10}$, C$_{1-11}$, C$_{1-12}$, C$_{2-3}$, C$_{2-4}$, C$_{2-5}$, C$_{2-6}$, C$_{2-7}$, C$_{2-8}$, C$_{2-9}$, C$_{2-10}$, C$_{2-11}$, C$_{2-12}$, C$_{3-4}$, C$_{3-5}$, C$_{3-6}$, C$_{3-7}$, C$_{3-8}$, C$_{3-9}$, C$_{3-10}$, C$_{3-11}$, C$_{3-12}$, C$_{4-5}$, C$_{4-6}$, C$_{5-6}$, C$_{5-7}$, C$_{5-8}$, C$_{5-9}$, C$_{5-10}$, C$_{5-11}$, C$_{5-12}$, C$_{6-7}$, C$_{6-8}$, C$_{6-9}$, C$_{6-10}$, C$_{6-11}$, C$_{6-12}$, C$_{7-8}$, C$_{7-9}$, C$_{7-10}$, C$_{7-11}$, C$_{7-12}$, C$_{8-9}$, C$_{8-10}$, C$_{8-11}$, C$_{8-12}$, C$_{9-10}$, C$_{9-11}$, C$_{9-12}$, C$_{10-11}$, C$_{10-12}$, and C$_{11-12}$. For example, C$_{1-12}$ alkyl includes, but is not limited to, methyl, ethyl, n-propyl, isopropyl, n-butyl, isobutyl, sec-butyl, tent-butyl, n-pentyl, isopentyl, n-hexyl, n-heptyl, n-octyl, n-nonyl, n-decyl, n-undecyl, n-dodecyl, etc. Alkyl can also refer to alkyl groups having up to 20 carbons atoms, such as, but not limited to tridecyl, tetradecyl, pentadecyl, hexadecyl, heptadecyl and octadecyl, etc.

"Pharmaceutically acceptable complex" as used herein refers to a complex including a compound of formula (I) and at least one complexing agent. The term "pharmaceutically acceptable" means approved by a regulatory agency of the Federal or a state government or listed in the U.S. Pharmacopeia or other generally recognized pharmacopeia for use in animals, and more particularly in humans. The complexing agents have the function to form a complex structure with the compound of formula (I) through non-covalent secondary interactions. The secondary interactions can form through electrostatic interactions such as ionic interactions, H-bonding, dipole-dipole interactions, dipole-induced dipole interactions, London dispersion forces, π-π interactions, and hydrophobic interactions. The pharmaceutically acceptable complex of the compound of formula (I) includes a pharmaceutically acceptable salt and/or solvate thereof.

"Solvate" refers to a compound provided herein or a salt thereof, that further includes a stoichiometric or non-stoichiometric amount of solvent bound by non-covalent intermolecular forces. Where the solvent is water, the solvate is a hydrate.

"Hydrate" refers to a compound that is complexed with water molecule. The compounds of the present invention can be complexed with ½ water molecule or from 1 to 10 water molecules.

"Peptide-p-nitroanilide" or "peptide-pNA" as used herein refers to a peptide substrate having 4 to 6 amino acids joined by peptide bonds and a p-nitroanilide group at the C-terminus. Examples of peptide-pNA substrates in the present invention includes Tyr-Arg-Ser-Arg-pNA (SEQ ID NO. 1) and Lys-His-Leu-Tyr-pNA (SEQ ID NO. 2).

"Composition" as used herein is intended to encompass a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

"Pharmaceutically acceptable carrier or excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. Pharmaceutical excipients useful in the present invention for transdermal/topical delivery include, but are not limited to, enhancers, solubilizers, antioxidants, plastisizers, thickeners, polymers, and pressure sensitive adhesives. One of skill in the art will recognize that other pharmaceutical excipients are useful in the present invention.

"$IC_{50}$" refers to an amount, concentration or dosage of a particular test compound that achieves a 50% inhibition of a maximal response in an assay that measures such response.

"Inhibition", "inhibits" and "inhibitor" refer to a compound that prohibits or a method of prohibiting, a specific action or function.

"Administering" refers to topical administration, for example as a lotion, a spray, an ointment, a cream, a gel, a paste, or a patch.

"Topical" means application of a suitable compound (e.g. active agent) or composition comprising a compound (e.g. active agent) to the skin to treat diseases or conditions, for example genodermatoses. In some embodiments, "topical" means application of a suitable compound (e.g. active agent) or composition comprising a compound (e.g. active agent) to the skin with adequate penetration of the epidermis or dermis to treat the genodermatosis. In some embodiments of topical application, the compound or composition penetrates the epidermis or dermis without significant systemic exposure nor intent to treat or prevent a disease of another organ system. In some embodiments of topical application, the compound or composition is delivered by transdermal across the skin for systemic distribution. Examples include transdermal patches used for drug delivery.

"Treat", "treating" and "treatment" refer to any indicia of success in the treatment or amelioration of an injury, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation.

"Patient" or "subject" refers to a living organism suffering from or prone to a disease or condition that can be treated by administration of a pharmaceutical composition as provided herein. Non-limiting examples include humans, other mammals, bovines, rats, mice, dogs, monkeys, goat, sheep, cows, deer, and other non-mammalian animals. In some embodiments, the patient is human.

"Therapeutically effective amount" refers to an amount of a compound or of a pharmaceutical composition useful for treating or ameliorating an identified disease or condition, or for exhibiting a detectable therapeutic or inhibitory effect. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

"A," "an," or "a(n)", when used in reference to a group of substituents or "substituent group" herein, mean at least one. For example, where a compound is substituted with "an" alkyl or aryl, the compound is optionally substituted with at least one alkyl and/or at least one aryl, wherein each alkyl and/or aryl is optionally different. In another example, where a compound is substituted with "a" substituent group, the compound is substituted with at least one substituent group, wherein each substituent group is optionally different.

III. Compounds

In one aspect, the present invention provides a compound represented by formula (I):

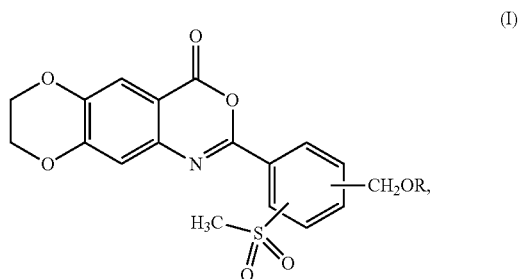

(I)

or a pharmaceutically acceptable complex thereof; wherein R is H or a member selected from the group consisting of —$R^1$ and —$C(O)R^{1a}$, wherein $R^1$ is $C_{1-12}$ alkyl, and $R^{1a}$ is H or $C_{1-12}$ alkyl.

The methylsulfonyl (—SO$_2$CH$_3$) group in formula (I) can be at ortho-, meta-, or para-position in relation to the moiety of 7,8-dihydro-4H-[1,4]dioxino[2',3':4,5]benzo[1,2-d][1,3]oxazin-4-one. In some embodiments, the —SO$_2$CH$_3$ group is at the ortho-position in relation to the moiety of 7,8-dihydro-4H-[1,4]dioxino[2',3':4,5]benzo[1,2-d][1,3]oxazin-4-one.

The —CH$_2$OR group in formula (I) can be at an ortho-, meta-, or para- position in relation to the moiety of 7,8-dihydro-4H-[1,4]dioxino[2',3':4,5]benzo[1,2-d][1,3]oxazin-4-one. In some embodiments, the —CH$_2$OR group is at the meta-position in relation to the moiety of 7,8-dihydro-4H-[1,4]dioxino[2',3':4,5]benzo[1,2-d][1,3]oxazin-4-one. In some embodiments, the —CH$_2$OR group is at the para-position in relation to the moiety of 7,8-dihydro-4H-[1,4]dioxino[2',3':4,5]benzo[1,2-d][1,3]oxazin-4-one.

In some embodiments, the compound is represented by formula (Ia):

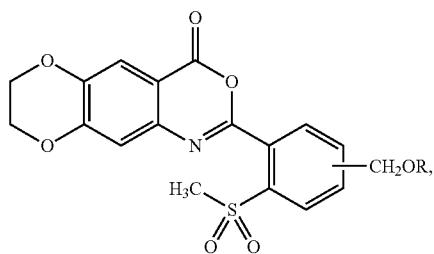

(Ia)

wherein R is as defined and described for formula (I).

In some embodiments of formula (Ia), the —CH$_2$OR group can be at an ortho-, meta-, or para-position in relation to the —SO$_2$CH$_3$ group. In some embodiments, the —CH$_2$OR group is at the meta-position in relation to the —SO$_2$CH$_3$ group. In some embodiments, the —CH$_2$OR group is at the para-position in relation to the —SO$_2$CH$_3$ group.

In some embodiments, the compound is represented by formula (Ib):

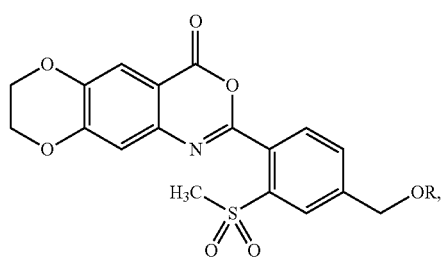

(Ib)

wherein R is as defined and described for formula (I).

In some embodiments, the compound is represented by formula (Ic):

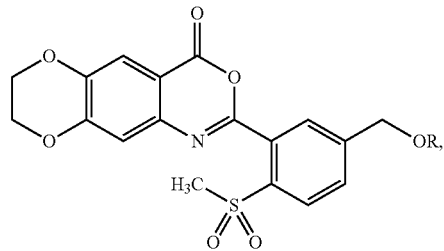

(Ic)

wherein R is as defined and described for formula (I).

With reference to any one of formulae (I), (Ia), (Ib), and (Ic), in some embodiments, R is H.

In some embodiments, the compound is represented by the formula:

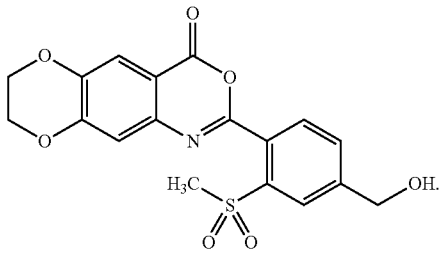

In some embodiments, the compound is represented by the formula:

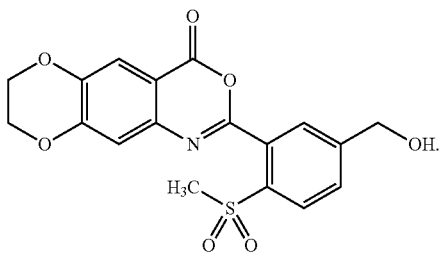

With reference to any one of formulae (I), (Ia), (Ib), and (Ic), in some embodiments, R is a member selected from the group consisting of —R$^1$ and —C(O)R$^{1a}$, wherein le is C$_{1-12}$ alkyl, and R$^{1a}$ is H or C$_{1-12}$ alkyl.

In some embodiments of any one of formulae (I), (Ia), (Ib), and (Ic), R is C$_{1-12}$ alkyl. In some embodiments, R is methyl, ethyl, n-propyl, isopropyl, n-butyl, isobutyl, sec-butyl, tent-butyl, n-pentyl, isopentyl, n-hexyl, n-heptyl, n-octyl, n-nonyl, n-decyl, n-undecyl, or n-dodecyl. In some embodiments, R is C$_{1-6}$ alkyl. In some embodiments, R is methyl, ethyl, n-propyl, isopropyl, n-butyl, isobutyl, sec-butyl, tent-butyl, n-pentyl, isopentyl, or n-hexyl. In some embodiments, R is methyl or ethyl. In some selected embodiments, R is methyl.

In some embodiments of any one of formulae (I), (Ia), (Ib), and (Ic), R is —C(O)R$^{1a}$, wherein R$^{1a}$ is H or C$_{1-12}$ alkyl. In some embodiments, R$^{1a}$ is H. In some embodiments, R$^{1a}$ is C$_{1-12}$ alkyl. In some embodiments, R$^{1a}$ is methyl, ethyl, n-propyl, isopropyl, n-butyl, isobutyl, sec-butyl, tent-butyl, n-pentyl, isopentyl, n-hexyl, n-heptyl, n-octyl, n-nonyl, n-decyl, n-undecyl, or n-dodecyl. In some embodiments, $R^{1a}$ is $C_{1-6}$ alkyl. In some embodiments, $R^{1a}$ is methyl, ethyl, n-propyl, isopropyl, n-butyl, isobutyl, sec-butyl, tent-butyl, n-pentyl, isopentyl, or n-hexyl. In some embodiments, $R^{1a}$ is methyl or ethyl. In some selected embodiments, $R^{1a}$ is methyl. In some embodiments, R is acetyl.

In some embodiments, the compound is represented by the formula:

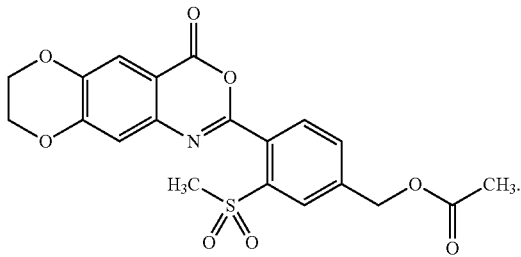 [SMILES: CC(=O)OCc1ccc(-c2nc3cc4c(cc3c(=O)o2)OCCO4)c(S(C)(=O)=O)c1]

In some embodiments, the compound is represented by the formula:

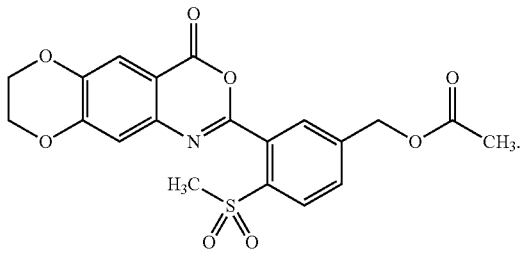 [SMILES: CC(=O)OCc1ccc(S(C)(=O)=O)c(-c2nc3cc4c(cc3c(=O)o2)OCCO4)c1]

Exemplified compounds of formula (I) are listed in Table 1.

TABLE 1

| Compounds of formula (I) | |
|---|---|
| No. | Structure |
| 1.001 | ![structure] |
| 1.002 | ![structure] |

Compounds in Other Forms

The compounds of the present invention may exit as complexes with at least one complexing agent. The complexing agents have the function to form a complex structure with the compound of formula (I) through non-covalent secondary interactions. The secondary interactions can form through electrostatic interactions such as ionic interactions, H-bonding, dipole-dipole interactions, dipole-induced dipole interactions, London dispersion forces, π-π interactions, and hydrophobic interactions. The pharmaceutically acceptable complex of the compound of formula (I) includes a pharmaceutically acceptable salt and/or solvate thereof. In some embodiments, the pharmaceutically acceptable complex of the compound of formula (I) is a pharmaceutically acceptable salt and/or solvate thereof. In some embodiments, the pharmaceutically acceptable complex of the compound of formula (I) is a pharmaceutically acceptable salt thereof. In some embodiments, the pharmaceutically acceptable complex of the compound of formula (I) is a pharmaceutically acceptable solvate thereof.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Unless otherwise stated, the compounds of the present invention may also contain unnatural proportions of atomic isotopes at one or more of the atoms that constitute such compounds. For example, the compounds of the present invention may be labeled with radioactive or stable isotopes, such as for example deuterium ($^{2}H$), tritium ($^{3}H$), iodine-125 ($^{125}I$), fluorine-18 ($^{18}F$), nitrogen-15 ($^{15}N$), oxygen-17 ($^{17}O$), oxygen-18 ($^{18}O$), carbon-13 ($^{13}C$), or carbon-14 ($^{14}C$). All isotopic variations of the compounds of the present invention, whether radioactive or not, are encompassed within the scope of the present invention.

The present invention provides compounds, which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

IV. Composition

In a second aspect, the present invention provides a pharmaceutical composition including the compound of formula (I) or a pharmaceutically acceptable complex thereof and a pharmaceutically acceptable carrier. In some embodiments, the pharmaceutical composition includes the compound of formula (Ia) or a pharmaceutically acceptable complex thereof and a pharmaceutically acceptable carrier. In some embodiments, the pharmaceutical composition includes the compound of formula (Ib) or a pharmaceutically acceptable complex thereof and a pharmaceutically acceptable carrier. In some embodiments, the pharmaceutical composition includes the compound of formula (Ic) or a pharmaceutically acceptable complex thereof and a pharmaceutically acceptable carrier.

The pharmaceutically acceptable complex of the compound of any one of formulae (I), (Ia), (Ib), and (Ic) is defined and described herein. The pharmaceutically acceptable complex of the compound of any one formulae (I), (Ia), (Ib), and (Ic) can include a pharmaceutically acceptable salt, and/or solvate thereof.

In some embodiments, the compound of any one of formulae (I), (Ia), (Ib), and (Ic) has the formula:

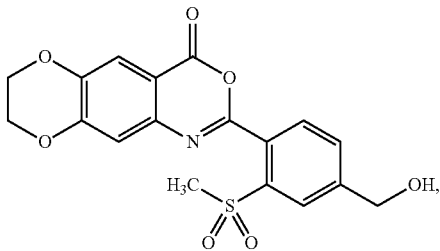 [SMILES: CS(=O)(=O)c1cc(CO)ccc1-c1nc2cc3c(cc2c(=O)o1)OCCO3]

or a pharmaceutically acceptable complex thereof.

In some embodiments, the compound of any one of formulae (I), (Ia), (Ib), and (Ic) has the formula:

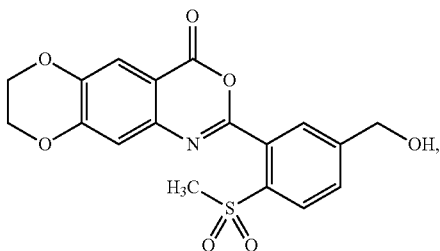 [SMILES: CS(=O)(=O)c1ccc(CO)cc1-c1nc2cc3c(cc2c(=O)o1)OCCO3]

or a pharmaceutically acceptable complex thereof.

The compounds provided herein can be formulated into pharmaceutical compositions using methods available in the art and those disclosed herein. Any of the compounds disclosed herein can be provided in the appropriate pharmaceutical composition and be administered by a suitable route of administration.

Administration of the compound described herein to a subject may be local or non-systemic, e.g., topical, intradermal, or intralesional. In some embodiments, the compound can be administered by topical administration. In some embodiments, the compound can be administered by intradermal administration. In some embodiments, the compound can be administered by intralesional administration, e.g., by intralesional injection.

The methods provided herein encompass administering pharmaceutical compositions containing at least one compound as described herein, including the compound of formula (I) if appropriate in a salt form or in a complex form, either used alone or in the form of a combination with one or more compatible and pharmaceutically acceptable carriers, such as diluents or adjuvants, or with another agent for the treatment of a genodermatosis where the subject is in need thereof.

In certain embodiments, the second agent can be formulated or packaged with the compound provided herein. Of course, the second agent will only be formulated with the compound provided herein when, according to the judgment of those of skill in the art, such co-formulation should not interfere with the activity of either agent or the method of administration. In certain embodiments, the compound provided herein and the second agent are formulated separately. They can be packaged together, or packaged separately, for the convenience of the practitioner of skill in the art.

In clinical practice the active agents provided herein may be administered by any conventional route, in particular topically, intradermally, intralesionally, orally, parenterally, rectally, or by inhalation (e.g. in the form of aerosols). In certain embodiments, the compound provided herein is administered topically, intradermally, or intralesionally. In certain embodiments, the compound provided herein is administered topically. In certain embodiments, the compound provided herein is administered intradermally. In certain embodiments, the compound provided herein is administered intralesionally.

Use may be made, as solid compositions for oral administration, of tablets, pills, hard gelatin capsules, powders or granules. In these compositions, the active product is mixed with one or more inert diluents or adjuvants, such as sucrose, lactose or starch.

These compositions can comprise substances other than diluents, for example a lubricant, such as magnesium stearate, or a coating intended for controlled release.

Use may be made, as liquid compositions for oral administration, of solutions which are pharmaceutically acceptable, suspensions, emulsions, syrups and elixirs containing inert diluents, such as water or liquid paraffin. These compositions can also comprise substances other than diluents, in certain embodiments, wetting, sweetening or flavoring products.

Use may be made, of compositions for topical administration as lotions, tinctures, creams, emulsions, gels or ointments. In these compositions, the active product is mixed with one or more inert excipients including water, acetone, ethanol, ethylene glycol, propylene glycol, polyethylene glycol, butane 1,3 diol, isopropyl myristate, isopropyl palmitate, mineral oil, and mixtures thereof.

The compositions for parenteral, intralesional, or intradermal administration can be emulsions or sterile solutions. Use may be made, as solvent or vehicle, of propylene glycol, a polyethylene glycol, vegetable oils, in particular olive oil, or injectable organic esters, in certain embodiments, ethyl oleate. These compositions can also contain adjuvants, in particular wetting, isotonizing, emulsifying, dispersing and stabilizing agents. Sterilization can be carried out in several ways, in certain embodiments, using a bacteriological filter, by radiation or by heating. They can also be prepared in the form of sterile solid compositions which can be dissolved at the time of use in sterile water or any other injectable sterile medium.

The compositions for rectal administration are suppositories or rectal capsules which contain, in addition to the active principle, excipients such as cocoa butter, semi-synthetic glycerides or polyethylene glycols.

The compositions can also be aerosols. For use in the form of liquid aerosols, the compositions can be stable sterile solutions or solid compositions dissolved at the time of use in apyrogenic sterile water, in saline or any other pharmaceutically acceptable vehicle. For use in the form of dry aerosols intended to be directly inhaled, the active principle is finely divided and combined with a water-soluble solid diluent or vehicle, in certain embodiments, dextran, mannitol or lactose.

In certain embodiments, a composition provided herein is a pharmaceutical composition or a single unit dosage form. Pharmaceutical compositions and single unit dosage forms provided herein comprise a prophylactically or therapeutically effective amount of one or more prophylactic or therapeutic agents (e.g., a compound provided herein, or other prophylactic or therapeutic agent), and a typically one or more pharmaceutically acceptable carriers or excipients. In a specific embodiment and in this context, the term "pharmaceutically acceptable" means approved by a regulatory agency of the Federal or a state government or listed in the U.S. Pharmacopeia or other generally recognized pharmacopeia for use in animals, and more particularly in humans. The term "carrier" includes a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water can be used as a carrier when the pharmaceutical composition is administered intravenously. Saline solutions and aqueous dextrose and glycerol solutions can also be employed as liquid carriers, particularly for injectable solutions. Examples of suitable pharmaceutical carriers are described in Remington: The Science and Practice of Pharmacy; Pharmaceutical Press; 22 edition (Sep. 15, 2012).

Typical pharmaceutical compositions and dosage forms comprise one or more excipients. Suitable excipients are well-known to those skilled in the art of pharmacy, and in certain embodiments, suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Whether a particular excipient is suitable for incorporation into a pharmaceutical composition or dosage form depends on a variety of factors well known in the art including, but not limited to, the way in which the dosage form will be administered to a subject and the specific active ingredients in the dosage form. The composition or single unit dosage form, if desired, can also contain minor amounts of wetting or emulsifying agents, or pH buffering agents.

Lactose free compositions provided herein can comprise excipients that are well known in the art and are listed, in certain embodiments, in the U.S. Pharmacopeia (USP 36—NF 31 S2). In general, lactose free compositions comprise an active ingredient, a binder/filler, and a lubricant in pharmaceutically compatible and pharmaceutically acceptable amounts. Exemplary lactose free dosage forms comprise an active ingredient, microcrystalline cellulose, pre gelatinized starch, and magnesium stearate.

Further encompassed herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long term storage in order to determine characteristics such as shelf life or the stability of formulations over time. See, e.g., Jens T. Carstensen, Drug Stability: Principles & Practice, 2d. Ed., Marcel Dekker, New York, 1995, pp. 379 80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine can be anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions can be packaged using materials known to prevent exposure to water such that they can be included in suitable formulary kits. In certain embodiments, suitable packaging include, but are not limited to, hermetically sealed foils, plastics, unit dose containers (e.g., vials), blister packs, and strip packs.

Further provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

The pharmaceutical compositions and single unit dosage forms can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Such compositions and dosage forms will contain a prophylactically or therapeutically effective amount of a prophylactic or therapeutic agent, in certain embodiments, in purified form, together with a suitable amount of carrier so as to provide the form for proper administration to the subject. The formulation should suit the mode of administration. In a certain embodiment, the pharmaceutical compositions or single unit dosage forms are sterile and in suitable form for administration to a subject, in certain embodiments, an animal subject, such as a mammalian subject, in certain embodiments, a human subject.

A pharmaceutical composition is formulated to be compatible with its intended route of administration. In certain embodiments, routes of administration include, but are not limited to, parenteral, e.g., intravenous, intradermal, subcutaneous, intramuscular, subcutaneous, oral, buccal, sublingual, inhalation, intranasal, transdermal, topical, transmucosal, intra-tumoral, intra-synovial and rectal administration. In certain embodiments, the route of administration is intradermal, topical, or intralesional administration. In certain embodiments, the route of administration is non-systemic administration. In a specific embodiment, the composition is formulated in accordance with routine procedures as a pharmaceutical composition adapted for intravenous, subcutaneous, intramuscular, oral, intranasal or topical administration to human beings. In an embodiment, a pharmaceutical composition is formulated in accordance with routine procedures for subcutaneous administration to human beings. Typically, compositions for intravenous administration are solutions in sterile isotonic aqueous buffer. Where necessary, the composition may also include a solubilizing agent and a local anesthetic such as lignocaine to ease pain at the site of the injection.

In certain embodiments, dosage forms include, but are not limited to: tablets; caplets; capsules, such as soft elastic gelatin capsules; cachets; troches; lozenges; dispersions; suppositories; ointments; cataplasms (poultices); pastes;

powders; dressings; creams; plasters; solutions; patches; aerosols (e.g., nasal sprays or inhalers); gels; liquid dosage forms suitable for oral or mucosal administration to a subject, including suspensions (e.g., aqueous or non-aqueous liquid suspensions, oil in water emulsions, or a water in oil liquid emulsions), solutions, and elixirs; liquid dosage forms suitable for parenteral administration to a subject; and sterile solids (e.g., crystalline or amorphous solids) that can be reconstituted to provide liquid dosage forms suitable for parenteral administration to a subject.

The composition, shape, and type of dosage forms provided herein will typically vary depending on their use. In certain embodiments, a dosage form used in the initial treatment of a genodermatosis may contain larger amounts of one or more of the active ingredients it comprises than a dosage form used in the maintenance treatment of the same disorder or disease. Similarly, a parenteral dosage form may contain smaller amounts of one or more of the active ingredients it comprises than an oral dosage form used to treat the same disease or disorder. These and other ways in which specific dosage forms encompassed herein will vary from one another will be readily apparent to those skilled in the art. See, e.g., Remington: The Science and Practice of Pharmacy; Pharmaceutical Press; 22 edition (Sep. 15, 2012).

Generally, the ingredients of compositions are supplied either separately or mixed together in unit dosage form, in certain embodiments, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

Typical dosage forms comprise a compound provided herein, or a pharmaceutically acceptable complex, solvate or hydrate thereof lie within the range of from about 0.1 mg to about 1000 mg per day, given as a single once-a-day dose in the morning or as divided doses throughout the day taken with food. Particular dosage forms can have about 0.1, 0.2, 0.3, 0.4, 0.5, 1.0, 2.0, 2.5, 5.0, 10.0, 15.0, 20.0, 25.0, 50.0, 100, 200, 250, 500 or 1000 mg of the active compound.

Oral Dosage Forms

Pharmaceutical compositions that are suitable for oral administration can be presented as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington: The Science and Practice of Pharmacy; Pharmaceutical Press; 22 edition (Sep. 15, 2012).

In certain embodiments, the oral dosage forms are solid and prepared under anhydrous diseases or disorders with anhydrous ingredients, as described in detail herein. However, the scope of the compositions provided herein extends beyond anhydrous, solid oral dosage forms. As such, further forms are described herein.

Typical oral dosage forms are prepared by combining the active ingredient(s) in an intimate admixture with at least one excipient according to conventional pharmaceutical compounding techniques. Excipients can take a wide variety of forms depending on the form of preparation desired for administration. In certain embodiments, excipients suitable for use in oral liquid or aerosol dosage forms include, but are not limited to, water, glycols, oils, alcohols, flavoring agents, preservatives, and coloring agents. In certain embodiments, excipients suitable for use in solid oral dosage forms (e.g., powders, tablets, capsules, and caplets) include, but are not limited to, starches, sugars, micro crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

In certain embodiments, a tablet can be prepared by compression or molding. Compressed tablets can be prepared by compressing in a suitable machine the active ingredients in a free flowing form such as powder or granules, optionally mixed with an excipient. Molded tablets can be made by molding in a suitable machine a mixture of the powdered compound moistened with an inert liquid diluent.

In certain embodiments, excipients that can be used in oral dosage forms include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre gelatinized starch, hydroxypropyl methyl cellulose, (e.g., Nos. 2208, 2906, 2910), microcrystalline cellulose, and mixtures thereof.

In certain embodiments, fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre gelatinized starch, and mixtures thereof. The binder or filler in pharmaceutical compositions is typically present in from about 50 to about 99 weight percent of the pharmaceutical composition or dosage form.

In certain embodiments, suitable forms of microcrystalline cellulose include, but are not limited to, the materials sold as AVICEL PH 101, AVICEL PH 103 AVICEL RC 581, AVICEL PH 105 (available from FMC Corporation, American Viscose Division, Avicel Sales, Marcus Hook, Pa.), and mixtures thereof. A specific binder is a mixture of microcrystalline cellulose and sodium carboxymethyl cellulose sold as AVICEL RC 581. Suitable anhydrous or low moisture excipients or additives include AVICEL PH 103™ and Starch 1500 LM.

Disintegrants are used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms. The amount of disintegrant used varies based upon the type of formulation, and is readily discernible to those of ordinary skill in the art. Typical pharmaceutical compositions comprise from about 0.5 to about 15 weight percent of disintegrant, specifically from about 1 to about 5 weight percent of disintegrant.

Disintegrants that can be used in pharmaceutical compositions and dosage forms include, but are not limited to, agar, alginic acid, calcium carbonate, microcrystalline cellulose, croscarmellose sodium, crospovidone, polacrilin potassium, sodium starch glycolate, potato or tapioca starch, pre gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, in certain embodiments, a syloid silica gel (AEROSIL 200, manufactured by W.R. Grace Co. of Baltimore, Md.), a coagulated aerosol of synthetic silica (marketed by Degussa Co. of Plano, Tex.), CAB O SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

Delayed Release Dosage Forms

Active ingredients such as the compounds provided herein can be administered by controlled release means or by delivery devices that are well known to those of ordinary skill in the art. In certain embodiments, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500; each of which is incorporated herein by reference in its entirety. Such dosage forms can be used to provide slow or controlled release of one or more active ingredients using, in certain embodiments, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus encompassed herein are single unit dosage forms suitable for oral administration such as, but not limited to, tablets, capsules, gel caps, and caplets that are adapted for controlled release.

All controlled release pharmaceutical products have a common goal of improving drug therapy over that achieved by their non-controlled counterparts. Ideally, the use of an optimally designed controlled release preparation in medical treatment is characterized by a minimum of drug substance being employed to cure or control the disease or disorder in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various diseases or disorders including, but not limited to, pH, temperature, enzymes, water, or other physiological diseases or disorders or compounds.

In certain embodiments, the drug may be administered using intravenous infusion, an implantable osmotic pump, a transdermal patch, liposomes, or other modes of administration. In certain embodiments, a pump may be used (see, Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, *Medical Applications of Controlled Release*, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

In certain embodiments, provided herein are parenteral dosage forms. In certain embodiments, parenteral dosage forms can be administered to subjects by various routes including, but not limited to, subcutaneous, intravenous (including bolus injection), intramuscular, and intra-arterial. In certain embodiments, parenteral dosage forms can be administered to subjects by various routes including, but not limited to, topical, intradermal, or intralesional. Because their administration typically bypasses subjects' natural defenses against contaminants, parenteral dosage forms are typically, sterile or capable of being sterilized prior to administration to a subject. In certain embodiments, parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. In certain embodiments, suitable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms.

Transdermal, Topical & Mucosal Dosage Forms

Also provided are transdermal, topical, and mucosal dosage forms. Transdermal, topical, and mucosal dosage forms include, but are not limited to, ophthalmic solutions, sprays, aerosols, creams, lotions, ointments, gels, solutions, emulsions, suspensions, or other forms known to one of skill in the art. See, e.g., Remington: The Science and Practice of Pharmacy; Pharmaceutical Press; 22 edition (Sep. 15, 2012); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels. Further, transdermal dosage forms include "reservoir type" or "matrix type" patches, which can be applied to the skin and worn for a specific period of time to permit the penetration of a desired amount of active ingredients.

The term "pharmaceutically acceptable carrier" refers to a pharmaceutically-acceptable material, composition or vehicle, such as a liquid or solid filler, diluent, excipient, solvent or encapsulating material, involved in carrying or transporting any subject composition or component thereof. Each carrier must be "acceptable" in the sense of being compatible with the subject composition and its components and not injurious to the patient. Suitable carriers (e.g., excipients and diluents) and other materials that can be used to provide transdermal, topical, and mucosal dosage forms encompassed herein are well known to those skilled in the pharmaceutical arts, and depend on the particular tissue to which a given pharmaceutical composition or dosage form will be applied. With that fact in mind, typical carriers include, but are not limited to, water, acetone, ethanol, ethylene glycol, propylene glycol, polyethylene glycol, butane 1,3 diol, isopropyl myristate, isopropyl palmitate, mineral oil, and mixtures thereof to form lotions, tinctures, creams, emulsions, gels or ointments, which are nontoxic and pharmaceutically acceptable. In some embodiments, materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations. Moisturizers or humectants can also be added to pharmaceutical compositions and dosage forms if desired. Examples of such additional ingredients are well known in the art. See, e.g., Remington: The Science and Practice of Pharmacy; Pharmaceutical Press; 22 edition (Sep. 15, 2012).

Depending on the specific tissue to be treated, additional components may be used prior to, in conjunction with, or subsequent to treatment with active ingredients provided. In certain embodiments, penetration enhancers can be used to assist in delivering the active ingredients to the tissue. Suitable penetration enhancers include, but are not limited to: acetone; various alcohols such as ethanol, oleyl, and tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water soluble or insoluble sugar esters such as Tween 80 (polysorbate 80) and Span 60 (sorbitan monostearate).

The pH of a pharmaceutical composition or dosage form, or of the tissue to which the pharmaceutical composition or dosage form is applied, may also be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients so as to improve delivery. In this regard, stearates can serve as a lipid vehicle for the formulation, as an emulsifying agent or surfactant, and as a delivery enhancing or penetration enhancing agent. Different complexes, salts, hydrates or solvates of the active ingredients can be used to further adjust the properties of the resulting composition.

Dosage and Unit Dosage Forms

In human therapeutics, a doctor will determine the posology which he considers most appropriate according to a preventive or curative treatment and according to the age, weight, stage of the disorder or disease and other factors specific to the subject to be treated. In certain embodiments, doses are from about 1 to about 1000 mg per day for an adult, or from about 5 to about 250 mg per day or from about 10 to 50 mg per day for an adult. In certain embodiments, doses are from about 5 to about 400 mg per day or 25 to 200 mg per day per adult. In certain embodiments, dose rates of from about 50 to about 500 mg per day are also contemplated.

In further aspects, provided are methods of treating a disease or disorder where the subject is in need thereof and/or a genodermatosis in a subject by administering, to a subject in need thereof, a therapeutically or prophylactically effective amount of a compound provided herein, or a pharmaceutically acceptable complex thereof. The amount of the compound or composition which will be therapeutically or prophylactically effective in the treatment of a disorder or one or more symptoms thereof will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the disorder, disease, or condition, the route of administration, as well as age, body, weight, response, and the past medical history of the subject. Effective doses may be extrapolated from dose-response curves derived from in vitro or animal model test systems.

In certain embodiments, exemplary doses of a composition include milligram or microgram amounts of the active compound per kilogram of subject or sample weight (e.g., about 10 micrograms per kilogram to about 50 milligrams per kilogram, about 100 micrograms per kilogram to about 25 milligrams per kilogram, or about 100 microgram per kilogram to about 10 milligrams per kilogram). For compositions provided herein, in certain embodiments, the dosage administered to a subject is 0.140 mg/kg to 3 mg/kg of the subject's body weight, based on weight of the active compound. In certain embodiments, the dosage administered to a subject is between 0.20 mg/kg and 2.00 mg/kg, between 0.30 mg/kg and 1.50 mg/kg, between 1 mg/kg and 100 mg/kg, between 5 mg/kg and 50 mg/kg, between 10 mg/kg and 50 mg/kg, between 20 mg/kg and 50 mg/kg, between 15 mg/kg and 40 mg/kg, between 15 mg/kg and 35 mg/kg, between 15 mg/kg and 30 mg/kg, between 25 mg/kg and 35 mg/kg, between 10 mg/kg and 30 mg/kg, between 10 mg/kg and 20 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, or about 50 mg/kg of of the subject's body weight.

In certain embodiments, the recommended daily dose range of a composition provided herein for the diseases or disorders described herein lie within the range of from about 0.1 mg to about 1000 mg per day, given as a single once-a-day dose or as divided doses throughout a day. In certain embodiments, the daily dose is administered twice daily in equally divided doses. In certain embodiments, a daily dose range should be from about 10 mg to about 200 mg per day, in other embodiments, between about 10 mg and about 150 mg per day, in further embodiments, between about 25 and about 100 mg per day. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

Different therapeutically effective amounts may be applicable for different diseases and conditions, as will be readily known by those of ordinary skill in the art. Similarly, amounts sufficient to prevent, manage, treat or ameliorate such disorders, but insufficient to cause, or sufficient to reduce, adverse effects associated with the composition provided herein are also encompassed by the herein described dosage amounts and dose frequency schedules. Further, when a subject is administered multiple dosages of a composition provided herein, not all of the dosages need be the same. In certain embodiments, the dosage administered to the subject may be increased to improve the prophylactic or therapeutic effect of the composition or it may be decreased to reduce one or more side effects that a particular subject is experiencing.

In certain embodiments, the dosage of the composition provided herein, based on weight of the active compound, administered to prevent, treat, manage, or ameliorate a disorder, or one or more symptoms thereof in a subject is 0.1 mg/kg, 1 mg/kg, 2 mg/kg, 3 mg/kg, 4 mg/kg, 5 mg/kg, 6 mg/kg, 10 mg/kg, or 15 mg/kg or more of a subject's body weight. In another embodiment, the dosage of the composition or a composition provided herein administered to prevent, treat, manage, or ameliorate a disorder, or one or more symptoms thereof in a subject is a unit dose of 0.1 mg to 200 mg, 0.1 mg to 100 mg, 0.1 mg to 50 mg, 0.1 mg to 25 mg, 0.1 mg to 20 mg, 0.1 mg to 15 mg, 0.1 mg to 10 mg, 0.1 mg to 7.5 mg, 0.1 mg to 5 mg, 0.1 to 2.5 mg, 0.25 mg to 20 mg, 0.25 to 15 mg, 0.25 to 12 mg, 0.25 to 10 mg, 0.25 mg to 7.5 mg, 0.25 mg to 5 mg, 0.5 mg to 2.5 mg, 1 mg to 20 mg, 1 mg to 15 mg, 1 mg to 12 mg, 1 mg to 10 mg, 1 mg to 7.5 mg, 1 mg to 5 mg, or 1 mg to 2.5 mg.

In certain embodiments, treatment or prevention can be initiated with one or more loading doses of a compound or composition provided herein followed by one or more maintenance doses. In such embodiments, the loading dose can be, for instance, about 60 to about 400 mg per day, or about 100 to about 200 mg per day for one day to five weeks. The loading dose can be followed by one or more maintenance doses. In certain embodiments, each maintenance does is, independently, about from about 10 mg to about 200 mg per day, between about 25 mg and about 150 mg per day, or between about 25 and about 80 mg per day. Maintenance doses can be administered daily and can be administered as single doses, or as divided doses.

In certain embodiments, a dose of a compound or composition provided herein can be administered to achieve a steady-state concentration of the active ingredient in blood or serum of the subject. The steady-state concentration can be determined by measurement according to techniques available to those of skill or can be based on the physical characteristics of the subject such as height, weight and age. In certain embodiments, a sufficient amount of a compound or composition provided herein is administered to achieve a steady-state concentration in blood or serum of the subject of from about 300 to about 4000 ng/mL, from about 400 to about 1600 ng/mL, from about 600 to about 1200 ng/mL. In certain embodiments, a sufficient amount of a compound or composition provided herein is administered topically to achieve a steady-state concentration in blood or serum of the subject of from about 0.01 to about 300 ng/mL, from about 0.01 to about 100 ng/mL, from about 0.01 to about 10 ng/mL, from about 0.01 to about 1 ng/mL, from about 0.01 to about 0.1 ng/mL, or from about 0.01 to about 0.05 ng/mL. In some embodiments, loading doses can be administered to achieve steady-state blood or serum concentrations of about 1200 to about 8000 ng/mL, or about 2000 to about 4000 ng/mL for one to five days. In some embodiments, loading doses can be administered topically to achieve steady-state blood or serum concentrations of from about 0.05 to about 1200 ng/mL, from about 0.05 to about 100 ng/mL, from about 0.05 to about 10 ng/mL, from about 0.05 to about 1 ng/mL, from about 0.05 to about 0.5 ng/mL, or from about 0.05 to about 0.1 ng/mL for one to five days. In certain embodiments, maintenance doses can be administered to achieve a steady-state concentration in blood or serum of the subject of from about 300 to about 4000 ng/mL, from about 400 to about 1600 ng/mL, or from about 600 to about 1200 ng/mL. In certain embodiments, maintenance doses can be administered topically to achieve a steady-state concentration in blood or serum of the subject of about 0.01 to about 300 ng/mL, from about 0.01 to about 100 ng/mL, from about 0.01 to about 10 ng/mL, from about 0.01 to about 1 ng/mL, from about 0.01 to about 0.1 ng/mL, or from about 0.01 to about 0.05 ng/mL.

In certain embodiments, administration of the same composition may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In certain aspects, provided herein are unit dosages comprising a compound, or a pharmaceutically acceptable complex thereof, in a form suitable for administration. Such forms are described in detail herein. In certain embodiments, the unit dosage comprises 1 to 1000 mg, 5 to 250 mg or 10 to 50 mg active ingredient. In particular embodiments, the unit dosages comprise about 1, 5, 10, 25, 50, 100, 125, 250, 500 or 1000 mg active ingredient. Such unit dosages can be prepared according to techniques familiar to those of skill in the art.

The dosage may vary within a range depending upon the dosage form employed and the route of administration utilized. For any compound, the therapeutically effective dose can be estimated initially from cell culture assays. A dose may be formulated in animal models to achieve a level in the skin with the lesion, e.g., Netherton Syndrome, or a skin disease mediated by KLK proteases) that includes the $IC_{50}$ (i.e., the concentration of the test compound that achieves a half-maximal inhibition of symptoms) as determined in cell culture. Such information can be used to more accurately determine useful doses in humans. In addition, levels in plasma may be measured, for example, by high performance liquid chromatography, in order to ascertain systemic exposure.

It should also be understood that a specific dosage and treatment regimen for any particular patient will depend upon a variety of factors, including the activity of the specific compound employed, the age, the size of the lesion, number of lesions, general health, sex, diet, time of administration, drug combination, and the judgment of the treating physician and the severity of the particular disease being treated. The amount of the compound of formula (I) described herein, in the composition will also depend upon the particular compound of formula (I) in the composition.

In some embodiments, the topical dose is about 0.01 µg/cm², about 0.05 µg/cm², about 0.1 µg/cm², about 0.15 µg/cm², about 0.2 µg/cm², about 0.3 µg/cm², about 0.4µg/cm², about 0.5 µg/cm², about 0.6 µg/cm², about 0.7 µg/cm², about 0.8 µg/cm², or about 0.9 µg/cm²; or is within about 0.01-0.03 µg/cm², about 0.03-0.05 µg/cm², about 0.05-0.1 µg/cm², about 0.1-0.3 µg/cm², about 0.3-0.5 µg/cm², about 0.5-0.8 µg/cm², about 0.8-1.0 µg/cm², about 1-10 µg/cm², about 10-20 µg/cm², about 20-30 µg/cm², about 30-40 µg/cm², about 40-50 µg/cm², about 50-60 µg/cm², about 60-70 µg/cm², about 70-80 µg/cm², about 80-90 µg/cm², about 90-100 µg/cm², about 100-125 µg/cm², about 125-150 µg/cm², about 150-175 µg/cm², about 175-200 µg/cm², about 200-250 µg/cm², about 250-300 µg/cm², about 300-350 µg/cm², about 350-400 µg/cm², about 400-450 µg/cm², about 450-500 µg/cm², about 500-550 µg/cm², about 550-600 µg/cm², about 600-650 µg/cm², about 650-700 µg/cm², about 700-750 µg/cm², about 750-800 µg/cm², about 800-850 µg/cm², about 850-900 µg/cm², about 900-950 µg/cm², or about 950-1000 µg/cm².

In some embodiments, the topical dose is within about 0.5-1.0 mg/cm², 1.0-1.5 mg/cm², 1.5-2.0 mg/cm², 2.5-2.5 mg/cm², 3.0-3.5 mg/cm², 3.5-5.0 mg/cm², 5.0-7.5 mg/cm², 7.5-10 mg/cm², 1-10 mg/cm², about 10-20 mg/cm², about 20-30 mg/cm², about 30-40 mg/cm², about 40-50 mg/cm², about 50-60 mg/cm², about 60-70 mg/cm², about 70-80 mg/cm², about 80-90 mg/cm², about 90-100 mg/cm², about 100-125 mg/cm², about 125-150 mg/cm², about 150-175 mg/cm², about 175-200 mg/cm², about 200-250 mg/cm², about 250-300 mg/cm², about 300-350 mg/cm², about 350- 400 mg/cm², about 400-450 mg/cm², about 450-500 mg/cm², about 500-550 mg/cm², about 550-600 mg/cm², about 600-650 mg/cm², about 650-700 mg/cm², about 700-750 mg/cm², about 750-800 mg/cm², about 800-850 mg/cm², about 850-900 mg/cm², about 900-950 mg/cm², or about 950-1000 mg/cm².

V. Methods

In a third aspect, provided herein is a method for treating a skin disease associated with proteolytic activity of one or more KLK proteases where the subject is in need thereof. The method includes administering the subject with a therapeutically effective amount of the compound of formula (I) or a pharmaceutically acceptable complex thereof, or the pharmaceutical composition including the compound of formula (I) or a pharmaceutically acceptable complex thereof.

In some embodiments, the compound of formulae (I) has the formula:

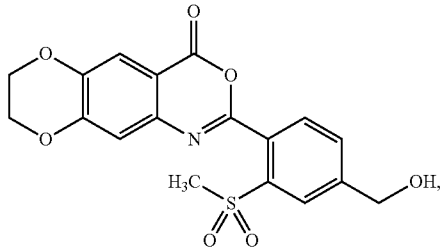 [SMILES: CS(=O)(=O)c1cc(CO)ccc1-c1nc2cc3c(cc2c(=O)o1)OCCO3]

or a pharmaceutically acceptable complex thereof.

In some embodiments, the compound of formulae (I) has the formula:

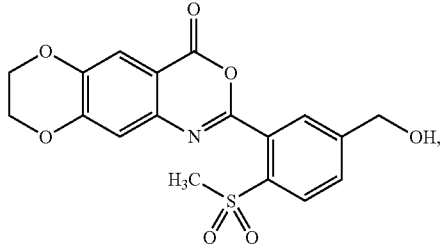 [SMILES: CS(=O)(=O)c1ccc(CO)cc1-c1nc2cc3c(cc2c(=O)o1)OCCO3]

or a pharmaceutically acceptable complex thereof.

The pharmaceutically acceptable complex of the compound of formula (I) is defined and described herein. The pharmaceutically acceptable complex of the compound of formula (I) can include a pharmaceutically acceptable salt, and/or solvate thereof.

In some embodiments, the skin disease is a genodermatosis. In some embodiments, the genodermatosis is Netherton Syndrome.

In some embodiments, the subject has truncated loss-of-function mutations of the serine protease inhibitor Kazal-type 5 (SPINK5). In some embodiments, the subject has a LEKTI (lymphoepithelial Kazal-type inhibitor) loss-of-function. In some embodiments, the subject has overexpression of one or more kallikrein (KLK) serine proteases. In some embodiments, the subject has overexpression of one or more KLK5, KLK7, and KLK14 proteases. In some embodiments, the subject has overexpression of KLK5 protease. In some embodiments, the subject has overexpression of KLK7 protease. In some embodiments, the subject has overexpression of KLK14 protease. In some embodiments, the subject has overexpression of KLK5 and KLK7 proteases. In some embodiments, the subject has overexpression of KLK5, KLK7, and KLK14 proteases. In some embodiments, the subject has elevated proteolytic activity of one or more kallikrein (KLK) serine proteases. In some embodiments, the subject has elevated proteolytic activity of one or more KLK5, KLK7, and KLK14 proteases. In some embodiments, the subject has elevated proteolytic activity of KLK5 protease. In some embodiments, the subject has elevated proteolytic activity of KLK7 protease. In some embodiments, the subject has elevated proteolytic activity of KLK14 protease. In some embodiments, the subject has elevated proteolytic activity of KLK5 and KLK7 proteases. In some embodiments, the subject has elevated proteolytic activity of KLK5, KLK7, and KLK14 proteases.

In some embodiments, provided herein is a method for treating Netherton Syndrome where the subject is in need thereof. The method includes administering the subject with a therapeutically effective amount of the compound of formula (I) or a pharmaceutically acceptable complex thereof, or the pharmaceutical composition including the compound of formula (I) or a pharmaceutically acceptable complex thereof.

In some embodiments, provided herein is a method for treating a genodermatosis where the subject is in need thereof and the genodermatosis is mediated by one or more KLK proteases. The method includes administering the subject with a therapeutically effective amount of the compound of formula (I) or a pharmaceutically acceptable complex thereof, or the pharmaceutical composition including the compound of formula (I) or a pharmaceutically acceptable complex thereof. In some embodiments, the genodermatosis is mediated by KLK5 protease, KLK7 protease, KLK14 protease, or combinations thereof. In some embodiments, the genodermatosis is mediated by KLK5 protease. In some embodiments, the genodermatosis is mediated by KLK7 protease. In some embodiments, the genodermatosis is mediated by KLK14 protease. In some embodiments, the genodermatosis is mediated by both KLK5 and KLK7 proteases. In some embodiments, the genodermatosis is mediated by KLK5, KLK7, and KLK14 proteases. In some embodiments, the genodermatosis is Netherton Syndrome.

In some embodiments, provided herein is a method for treating a genodermatosis in a subject by inhibiting proteolytic activity of one or more KLK proteases. The method includes administering the subject with a therapeutically effective amount of the compound of formula (I) or a pharmaceutically acceptable complex thereof, or the pharmaceutical composition including the compound of formula (I) or a pharmaceutically acceptable complex thereof. In some embodiments, the compound of formula (I) inhibits proteolytic activity of one or more KLK proteases. In some embodiments, the compound of formula (I) inhibits proteolytic activity of KLK5 protease, KLK7 protease, KLK14 protease, or combinations thereof. In some embodiments, the compound of formula (I) inhibits proteolytic activity of KLK5 protease. In some embodiments, the compound of formula (I) inhibits proteolytic activity of KLK7 protease. In some embodiments, the compound of formula (I) inhibits proteolytic activity of KLK14 protease. In some embodiments, the compound of formula (I) inhibits proteolytic activity of KLK5 and KLK7 proteases. In some embodiments, the compound of formula (I) inhibits proteolytic activity of KLK5, KLK7, and KLK14 proteases. In some embodiments, the compound of formula (I) is a KLK5 inhibitor. In some embodiments, the compound of formula (I) is a KLK7 inhibitor. In some embodiments, the compound of formula (I) is a KLK14 inhibitor. In some embodiments, the compound of formula (I) is a dual KLK5/KLK7 inhibitor. In some embodiments, the genodermatosis is Netherton Syndrome.

In some embodiments, provided herein is a method for treating Netherton Syndrome in a subject by inhibiting proteolytic activity of one or more KLK proteases. The method includes administering to the subject a therapeutically effective amount of the compound of formula (I) or a pharmaceutically acceptable complex thereof, or the pharmaceutical composition including the compound of formula (I) or a pharmaceutically acceptable complex thereof. In some embodiments, the compound of formula (I) inhibits proteolytic activity of one or more KLK proteases. In some embodiments, the compound of formula (I) inhibits proteolytic activity of KLK5 protease, KLK7 protease, KLK14 protease, or combinations thereof. In some embodiments, the compound of formula (I) inhibits proteolytic activity of KLK5 protease. In some embodiments, the compound of formula (I) inhibits proteolytic activity of KLK7 protease. In some embodiments, the compound of formula (I) inhibits proteolytic activity of KLK14 protease. In some embodiments, the compound of formula (I) inhibits proteolytic activity of KLK5 and KLK7 proteases. In some embodiments, the compound of formula (I) inhibits proteolytic activity of KLK5, KLK7, and KLK14 proteases. In some embodiments, the compound of formula (I) is a KLK5 inhibitor. In some embodiments, the compound of formula (I) is a KLK7 inhibitor. In some embodiments, the compound of formula (I) is a KLK14 inhibitor. In some embodiments, the compound of formula (I) is a dual KLK5/KLK7 inhibitor.

The compounds of the present invention are useful for protecting the skin by inhibiting proteolytic activity of one or more KLK proteases and promoting healthy skin development. Thus, in a further aspect, provided herein is a method for treating a skin disease where the subject is in need thereof and the skin disease is mediated by one or more KLK proteases. The method includes administering the subject with a therapeutically effective amount of the compound of formula (I) or a pharmaceutically acceptable complex thereof, or the pharmaceutical composition including the compound of formula (I) or a pharmaceutically acceptable complex thereof. In some embodiments, the skin disease is mediated by KLK5 protease, KLK7 protease, KLK14 protease, or combinations thereof. In some embodiments, the skin disease is mediated by KLK5 protease. In some embodiments, the skin disease is mediated by KLK7 protease. In some embodiments, the skin disease is mediated by KLK14 protease. In some embodiments, the skin disease is mediated by both KLK5 and KLK7 proteases. In some embodiments, the skin disease is mediated by KLK5, KLK7, and KLK14 proteases. In some embodiments, the skin disease is a KLK-mediated disease selected from the group consisting of Netherton Syndrome, peeling skin syndrome, acne rosacea, psoriasis, eczema, and atopic dermatitis. In some embodiments, the KLK-mediated disease is Netherton Syndrome.

In some embodiments, provided herein is a method for treating a skin disease in a subject by inhibiting proteolytic activity of one or more KLK proteases. The method includes administering the subject with a therapeutically effective amount of the compound of formula (I) or a pharmaceutically acceptable complex thereof, or the pharmaceutical composition including the compound of formula (I) or a pharmaceutically acceptable complex thereof. In some embodiments, the compound of formula (I) inhibits proteolytic activity of one or more KLK proteases. In some embodiments, the compound of formula (I) inhibits proteolytic activity of KLK5 protease, KLK7 protease, KLK14 protease, or combinations thereof. In some embodiments, the compound of formula (I) inhibits proteolytic activity of KLK5 protease. In some embodiments, the compound of formula (I) inhibits proteolytic activity of KLK7 protease. In some embodiments, the compound of formula (I) inhibits proteolytic activity of KLK14 protease. In some embodiments, the compound of formula (I) inhibits proteolytic activity of KLK5 and KLK7 proteases. In some embodiments, the compound of formula (I) inhibits proteolytic activity of KLK5, KLK7, and KLK14 proteases. In some embodiments, the compound of formula (I) is a KLK5 inhibitor. In some embodiments, the compound of formula (I) is a KLK7 inhibitor. In some embodiments, the compound of formula (I) is a KLK14 inhibitor. In some embodiments, the compound of formula (I) is a dual KLK5/KLK7 inhibitor. In some embodiments, the skin disease is selected from the group consisting of Netherton Syndrome, peeling skin syndrome, acne rosacea, psoriasis, eczema, and atopic dermatitis. In some embodiments, the skin disease is Netherton Syndrome.

The compound of formula (I) or the pharmaceutical composition including the compound of formula (I) of the invention can be used for both prophylactic and therapeutic treatment of a skin disease or pathology, or other undesirable skin condition in a subject. For example, compositions of the invention may be used for preventing skin irritations, preventing rashes, promoting healing of skin tissue after a rash or irritation has occurred (i.e., building the epidermis and/or dermis layers of the skin), preventing and/or retarding atrophy of the skin, preventing and/or retarding the appearance of spider vessels and/or red blotchiness on the skin, preventing and/or retarding peeling in the skin, preventing and/or relieving itching in the skin, regulating skin texture (e.g., ameliorating peeling, roughness, swelling and soreness), and improving skin color (e.g., reducing redness).

Prophylactic or therapeutic treatment of a genodermatosis or a skin disease in a subject can be practiced by applying the compound of formula (I) or a pharmaceutical composition thereof in the form of a skin lotion, cream, gel, foam, ointment, paste, emulsion, spray, conditioner, tonic, patch, or the like that is preferably intended to be left on the skin. After applying the composition to the skin, it can be left on the skin for a period of at least about 15 minutes, or at least about 30 minutes, or at least about 1 hour, or for at least several hours, for example, at least about 2 hours, 3 hours, 6 hours, 12 hours, or 24 hours.

The compounds of the present invention are also useful for regulating in vitro desquamation by inhibiting protease activity of one or more KLK proteases in cell/tissue culture procedures. Thus, in an additional aspect, the invention provides a method for disaggregating cells or tissue in vitro, the method including the steps of exposing the cells or tissue to a KLK protease (e.g., KLK5, KLK7 and/or KLK14) followed by exposure to the compound of formula (I) or a pharmaceutically acceptable complex thereof of the present invention.

It will be appreciated that this method has application to cell culture procedures generally, where the method can be used to dissociate and detach cells for passage. Furthermore, this method can be used in the culturing of artificial skin, where the selective cleavage of cell-cell adhesion proteins by a KLK protease (e.g., KLK5, KLK7 and/or KLK14) in conjunction with regulation of such cleavage by the compound of formula (I), a pharmaceutically acceptable complex thereof, results in cells/tissue better suited for subsequent therapeutic uses.

In another aspect, provided herein is an in vitro assay for determining proteolytic activity of one or more KLK proteases in a skin. The method includes 1) preparing a skin extract; 2) exposing a substrate and the compound of formula (I) or a pharmaceutically acceptable complex thereof to the skin extract; and 3) determining a rate of proteolytic cleavage of the substrate. In some embodiments, the substrate is a peptide-p-nitroanilide (also referred as peptide-pNA). In some embodiments, the substrate is a dipeptide-pNA, tripeptide-pNA, tetrapeptide-pNA, pentapeptide-pNA, or hexapeptide-pNA. In some embodiments, the substrate is a tetrapeptide-pNA. In some embodiments, the substrate is Tyr-Arg-Ser-Arg-pNA (SEQ ID NO. 1) or Lys-His-Leu-Tyr-pNA (SEQ ID NO. 2). In some embodiments, the substrate is Tyr-Arg-Ser-Arg-pNA (SEQ ID NO. 1). In some embodiments, the substrate is Lys-His-Leu-Tyr-pNA (SEQ ID NO. 2). The skin extract can be a human skin extract or an animal skin extract (e.g., mouse). In some embodiments, the skin extract is a human skin extract.

VI. Examples

General Synthetic Methods

As used herein, the symbols and conventions used in these processes, schemes and examples, regardless of whether a particular abbreviation is specifically defined, are consistent with those used in the contemporary scientific literature, for example, the Journal of the American Chemical Society or the Journal of Biological Chemistry. Specifically, but without limitation, the following abbreviations may be used in the examples and throughout the specification: eq. (equivalent); g (grams); mg (milligrams); mL (milliliters); µL (microliters); mM (millimolar); µM (micromolar); Hz (Hertz); MHz (megahertz); mmol (millimoles); hr or hrs (hours); min (minutes); RT (room temperature); MS (mass spectrometry); ESI (electrospray ionization); TLC (thin layer chromatography); HPLC (high pressure liquid chromatography); THF (tetrahydrofuran); CDCl$_3$ (deuterated chloroform); AcOH (acetic acid); DCM (dichloromethane); DMW (demineralized water); DME (dimethoxyethane); DMF (N,N-dimethylformamide); DMSO (dimethylsulfoxide); DMSO-d$_6$ (deuterated dimethylsulfoxide); EtOAc (ethyl acetate); and MeOH (methanol).

For all of the following examples, standard work-up and purification methods known to those skilled in the art can be utilized. Unless otherwise indicated, all temperatures are expressed in ° C. (degrees Celsius). All reactions are conducted at room temperature unless otherwise noted. Synthetic methodologies illustrated herein are intended to exemplify the applicable chemistry through the use of specific examples and are not indicative of the scope of the disclosure.

Example 1

2-(4-(Hydroxymethyl)-2-(methylsulfonyl)phenyl)-7,8-dihydro-4H-[1,4]dioxino[2',3':4,5]benzo[1,2-d][1,3]oxazin-4-one (compound 1.001)

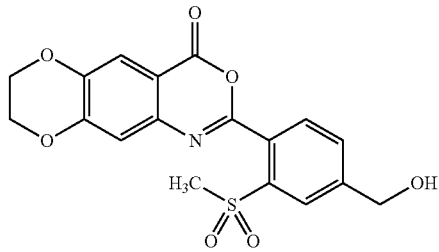 [SMILES: CS(=O)(=O)c1cc(CO)ccc1-c1nc2cc3c(cc2c(=O)o1)OCCO3]

Figure 3:
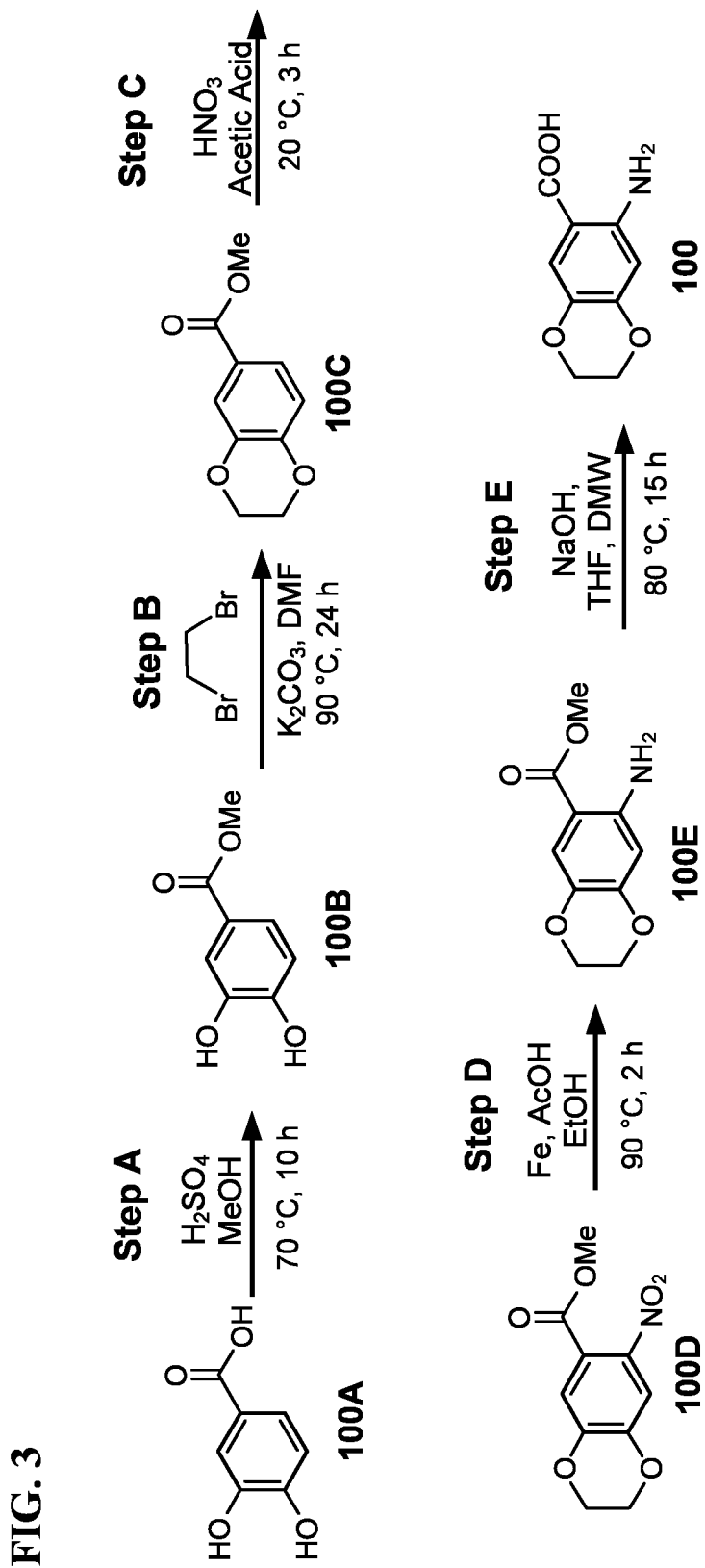
FIG. 3 shows a scheme for preparing the intermediate 100, which is used to prepare Compounds 1.001 and 1.002.
Figure 4A:
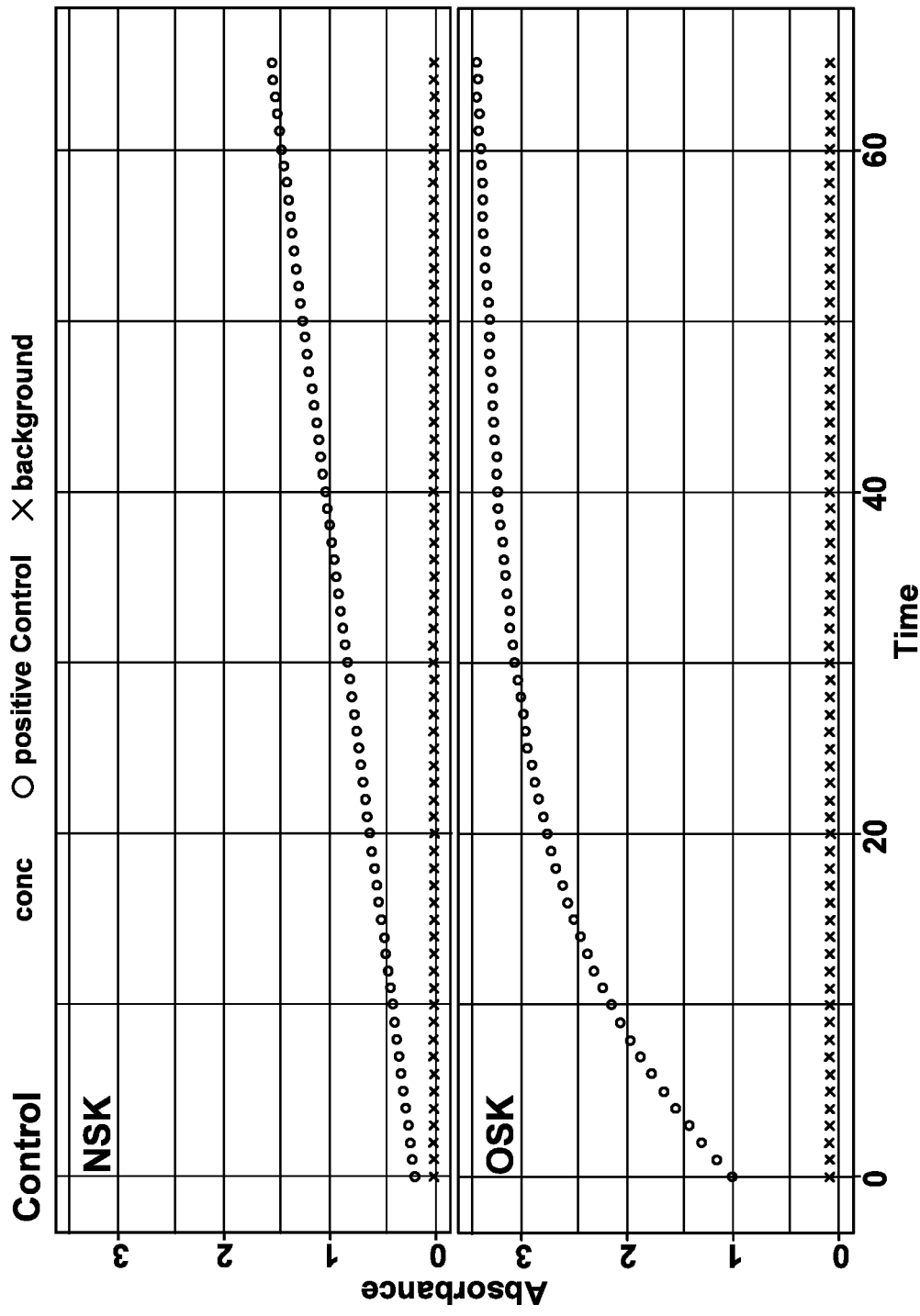
FIGS. 4A-4D show rates of proteolytic cleavage of KLK5 selective substrate in a skin extract assay by Compound 1.001, 1.002, or a known compound 14.
Figure 4B:
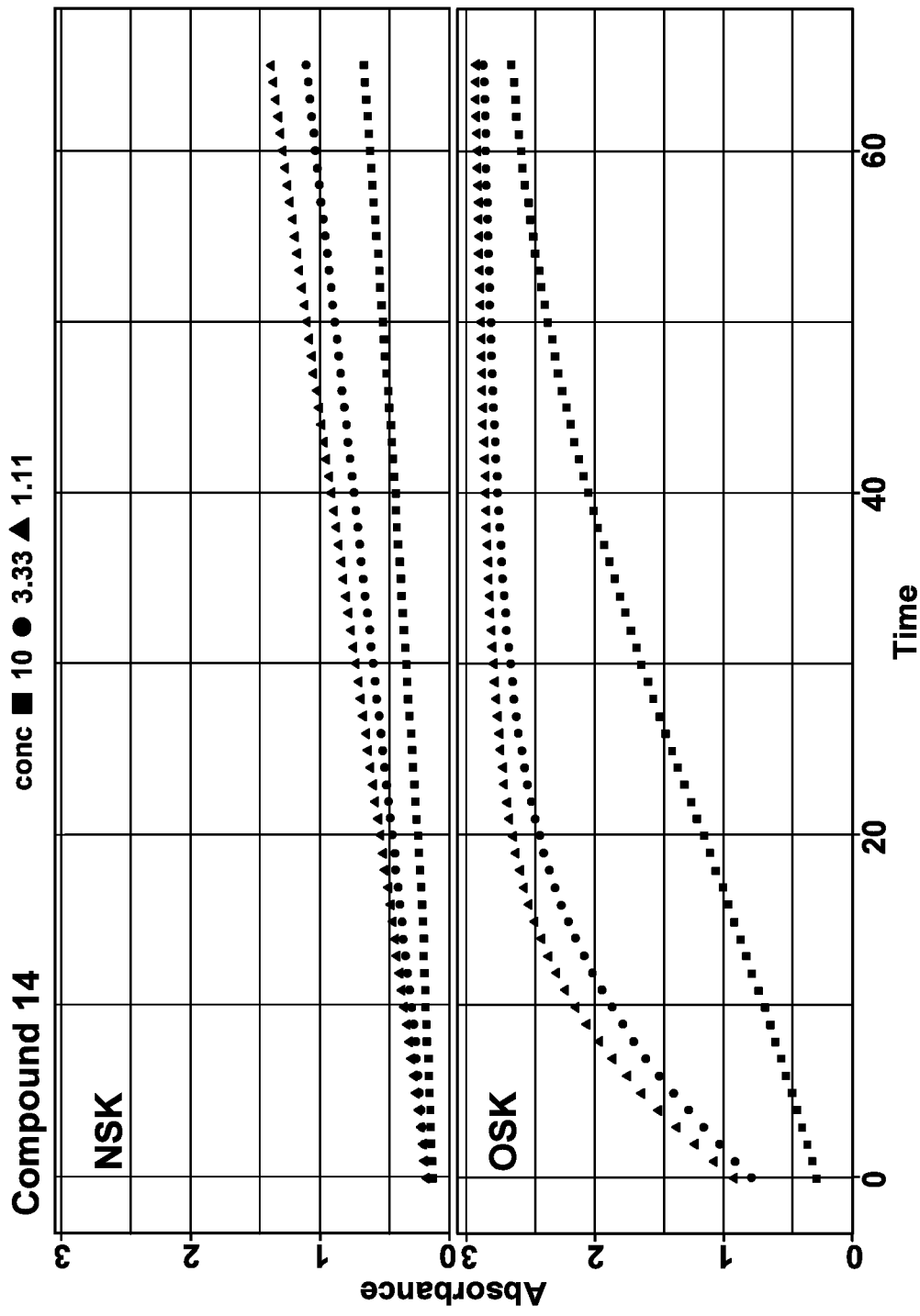
Figure 4C:
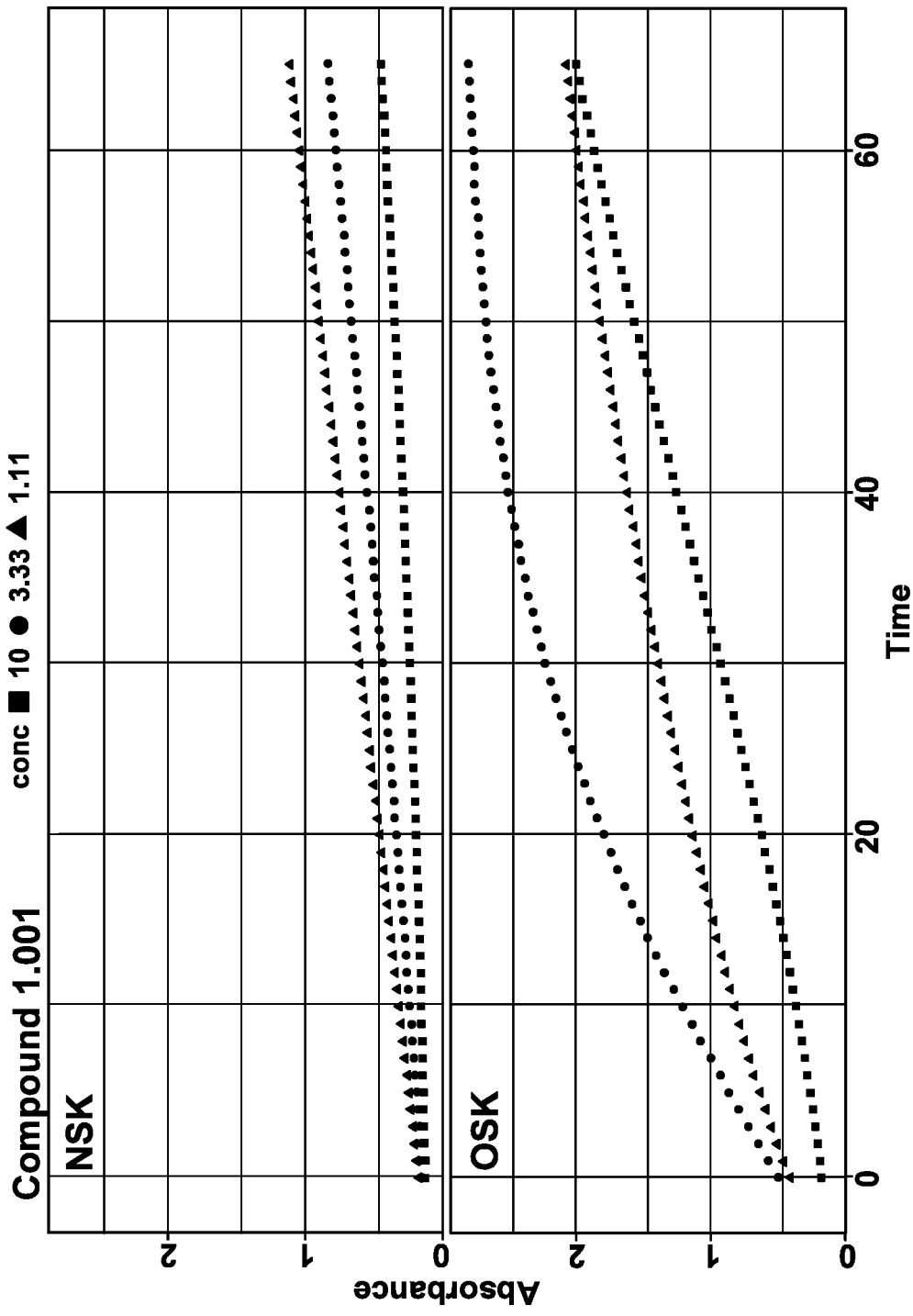
Figure 4D:
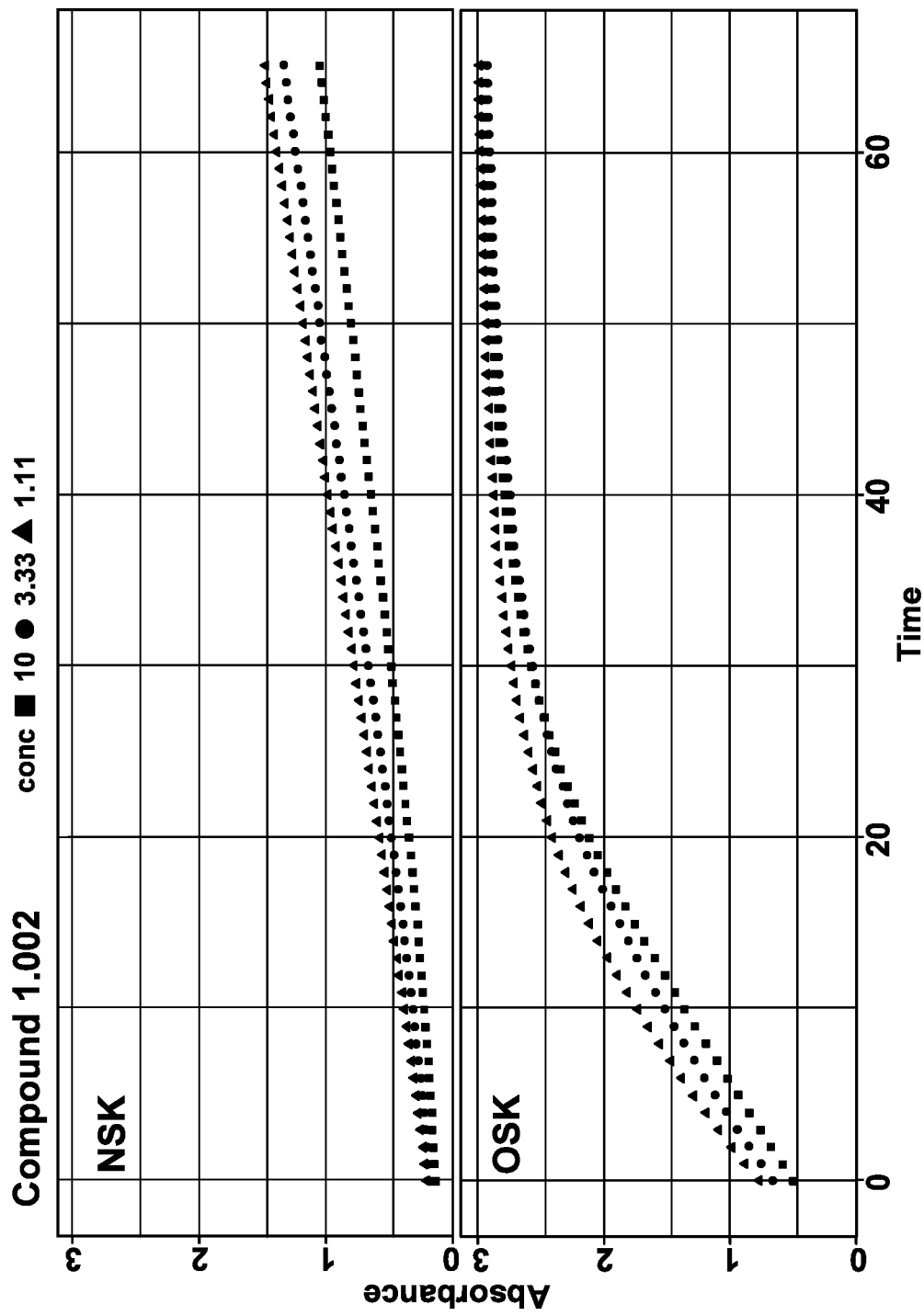

The synthesis of compound 1.001 is shown in FIG. 1. The synthesis of the intermediate 100 is illustrated in FIG. 3.

Step 1: 4-Bromo-2-mercaptobenzoic acid (Intermediate 102)

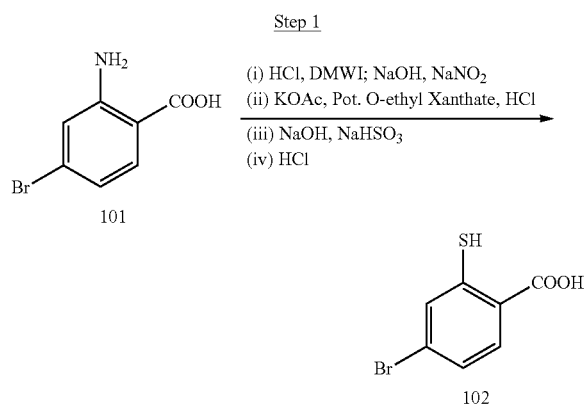

A mixture of conc. HCl (280.0 mL) and ice-cold water (280.0 mL) was added slowly to a stirred solution of 2-amino-4-bromobenzoic acid (101) (200.0 g, 926.0 mmol, 1.0 eq.), NaOH (37.0 g, 926.0 mmol, 1.0 eq.), and sodium nitrite (63.90 g, 926.0 mmol, 1.0 eq.) in DMW (4.0 L) in such a rate that the reaction temperature was maintained at 3-6° C. After the addition, the reaction mixture was stirred at 0° C. for 30 min, and then was neutralized with potassium acetate (454.0 g, 4.63 mol, 5.0 eq.). This solution was added to a preheated solution of potassium O-ethylxanthate (445.0 g, 2.78 mol, 3.0 eq.) in DMW (4.0 L) to 90° C. The reaction mixture was stirred at 90° C. for 30 min, cooled to 0° C., and acidified with conc. HCl (600.0 mL). The reaction mixture was basified with 20% NaOH (1750 ml), and heated to 85° C. for 2 h. To this mixture was added NaHSO$_3$ (96.30 g, 926.0 mmol, 1.0 eq.) in small portions, and the reaction mixture was heated to 85° C. for 10 min. The reaction mixture was filtered, cooled to 0° C., and acidified with conc. HCl (650.0 mL). The precipitated solid was collected by filtration, washed with DMW (500 mL) and then with n-hexane and air-dried to obtain intermediate 102 (216.0 g, 100.0%) as a light gray solid. $^1$HNMR (300 MHz, DMSO-d$_6$): δ 7.88 ppm (d, J=1.9 Hz, 1H), 7.81 ppm (t, J=7.4 Hz, 1H), 7.38 ppm (dd, J=8.4, 2.0 Hz, 1H). MS (ESI): m/z 232.8 (M−1).

Step 2: Methyl 4-bromo-2-(methylthio)benzoate (Intermediate 103)

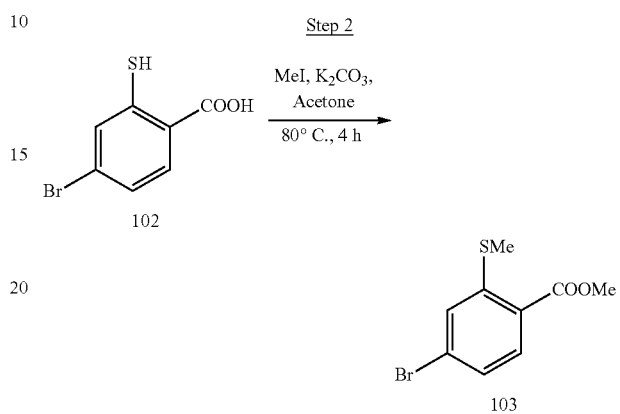

Potassium carbonate (896.0 g, 6.49 mol, 7.0 eq.) and methyl iodide (231.0 mL, 3.71 mol, 4.0 eq.) were added to a stirred solution of 4-bromo-2-mercaptobenzoic acid (102) (216.0 g, 927.0 mmol, 1.0 eq.) in DMF (3.24 L) at RT. The reaction mixture was heated to 80° C. and stirred at 80° C. for 20 h. The progress of the reaction was monitored by TLC (10% EtOAc in n-hexane) to ensure the completion of the reaction. DMW (2.5 L) was added and the product was extracted with ethyl acetate (2×2.5 L). The combined EtOAc extract was washed with DMW (2×2.5 L), brine (2.5 L), dried over sodium sulfate, filtered and filtrate was concentrated under vacuum to afford intermediate 103 (180 g, 74.40%) as a brown oil. $^1$HNMR (300 MHz, DMSO-d$_6$): δ7.83 ppm (d, J=8.3 Hz, 1H), 7.51-7.39 ppm (m, 2H), 3.83 ppm (s, 3H), 2.46 ppm (s, 3H).

Step 3: Methyl 4-bromo-2-(methylsulfonyl)benzoate (Intermediate 104)

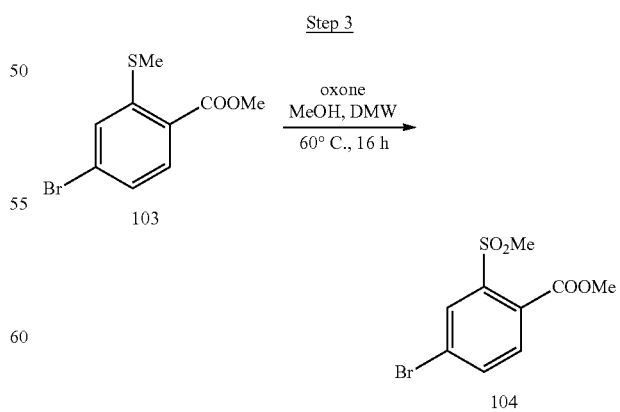

A solution of oxone (1.17 kg, 3.79 mol, 5.50 eq.) in DMW (4.50 L) was added to a stirred solution of methyl 4-bromo-2-(methylthio)benzoate (103) (180.0 g, 589 mmol, 1.0 eq.)

in methanol (3.60 L) at 0° C. The reaction mixture was stirred at 60° C. for 16 h. The progress of the reaction was monitored by TLC (30% EtOAc in n-hexane). About 40% of the solvent was removed by distillation then chilled DMW (4.50 L) was added to the reaction mixture and stirred for 15 minutes. The precipitated solid was collected by filtration to afford the wet product 104. The wet product was dried in a vacuum oven at below 50° C. to afford dried intermediate 104 (200 g, 99.0%) as an off white solid. $^1$HNMR (300 MHz, DMSO-$d_6$): δ 8 8.19-8.02 ppm (m, 2H), 7.73 ppm (d, J=8.1 Hz, 1H), 3.87 ppm (s, 3H), 3.42 ppm (s, 3H). MS (ESI): m/z 311.5 (M+18).

Step 4: 4-Bromo-2-(methyl sulfonyl)benzoic acid (Intermediate 105)

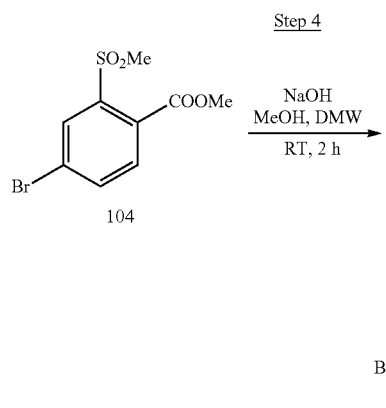

A solution of NaOH (192.0 g, 4.80 mol, 7.0 equiv.) in water (2.01 L) was added to a stirred solution of methyl 4-bromo-2-(methylsulfonyl)benzoate (104) (201.0 g, 0.68 mol, 1.0 equiv.) in methanol (2.01 L). The reaction mixture was stirred at RT for 3.0 h. The progress of the reaction was monitored by TLC (20% MeOH in DCM). The solvent was removed under reduced pressure. Ice cold DMW (1.5 L) was added to the residue and 5N HCl was added to adjust the pH to ~5. The precipitated solid was collected by filtration, washed with chilled water (1000 mL), dried to afford intermediate 105 (155.0 g, 81.0%) as an off white solid. $^1$H NMR (300 MHz, DMSO-$d_6$): 8.09 ppm (d, J=2.0 Hz, 1H), 8.04 ppm (dd, J=8.2, 2.0 Hz, 1H), 7.70 ppm (d, J=8.2 Hz, 1H), 3.44 ppm (s, 3H). MS (ESI): m/z 278.8 (M−1)

Step 5: 4-Bromo-2-(methyl sulfonyl)benzoyl chloride (Intermediate 106)

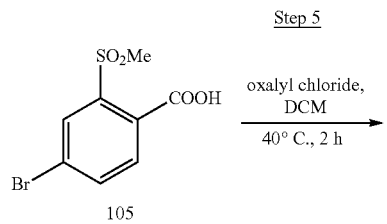

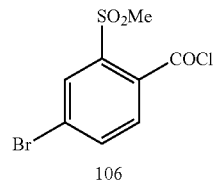

Thionyl chloride (68.4 mL, 940.0 mmol, 2.50 eq.) was added to stirred a solution of 4-bromo-2-(methylsulfonyl) benzoic acid (105) (105.0 g, 376.0 mmol, 1.0 eq.) in THF (1.05 L) followed by the addition DMF (1.37 mL, 18.80 mmol, 0.05 eq.) at RT. The reaction mixture was heated to 80° C. and stirred for 2 h. The progress of the reaction was monitored by TLC (50% EtOAc in n-hexane) to ensure the completion of the reaction. The solvent was removed under vacuum to obtain intermediate 106 (112.0 g). The crude material of intermediate 106 was used directly in step 6.

Step 6: 7-(4-Bromo-2-(methylsulfonyl)benzamido)-2,3-dihydrobenzo[b][1,4]dioxine-6-carboxylic acid (Intermediate 107)

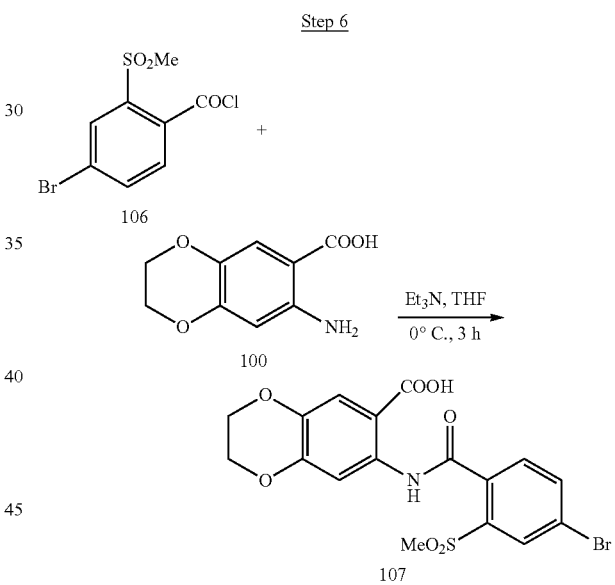

Triethylamine (103.0 mL, 753.0 mmol, 2.0 eq.) was added to stirred a solution of 7-amino-2,3-dihydrobenzo[b][1,4] dioxine-6-carboxylic acid (100) (60.20 g, 309.0 mmol, 0.82 eq.) in THF (1.68 L) at 0° C., then added a solution of 4-bromo-2-(methylsulfonyl)benzoyl chloride (106) (60.20 g, 309 mmol, 1.0 eq.) in THF (1.68 L) at 0° C. The reaction mixture was stirred at 0° C. for 10 minutes and then at RT for 2.5 h. The progress of the reaction was monitored by TLC (10% MeOH in DCM). 1N HCl was added to adjust the pH to 7. About 70% of THF was removed by distillation and the remaining residue was triturated with diethyl ether (250 mL) to precipitate the solid product. The solid was collected by filtration, washed with dietylether (50 mL) and dried to afford intermediate 107 (120.0 g, 69.90%) as a light brown solid.

Intermediate 100, 7-amino-2,3-dihydrobenzo[b][1,4]dioxine-6-carboxylic acid, was synthesized via steps A-E as described herein.

Step A: Methyl 3,4-dihydroxybenzoate (Intermediate 100B)

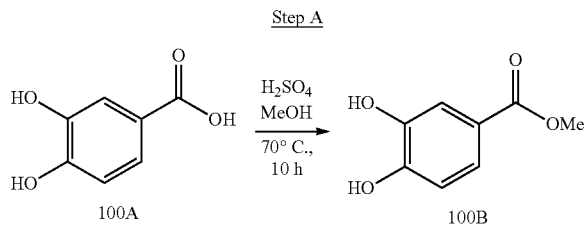 [SMILES: O=C(O)c1ccc(O)c(O)c1 ; COC(=O)c1ccc(O)c(O)c1]

Sulfuric acid (138.0 mL, 2.60 mol, 2.0 eq.) was added to stirred a solution of 3,4-dihydroxy benzoic acid (100A) (200.0 g, 1.30 mol, 1.0 eq.) in methanol (2.0 L). The reaction mixture was stirred at 80° C. for 15 h. The progress of the reaction was monitored by TLC (50% EtOAc in n-hexane). The solvent was removed by distillation under vacuum then DMW (1500 mL) was added and the product was extracted with ethyl acetate (3×1.5 L). The combined organic extract was washed with saturated solution of sodium bicarbonate (2000 mL) brine (1500 mL), dried over sodium sulfate and concentrated under vacuum to obtained the intermediate 100B (198.0 g, 90.70%) as an off white solid. $^1$H NMR (300 MHz, DMSO): δ 9.78 ppm (s, 1H), 9.37 ppm (s, 1H), 7.36-7.23 ppm (m, 2H), 6.81 ppm (d, J=8.2 Hz, 1H), 3.76 ppm (s, 3H).

Step B: Methyl 2,3-dihydrobenzo[b][1,4]dioxine-6-carboxylate (Intermediate 100C)

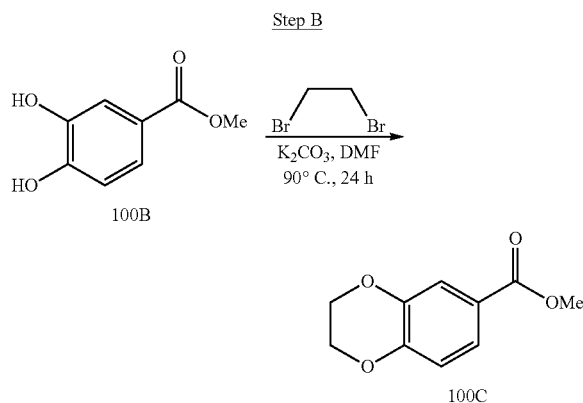

Potassium carbonate (405 g, 2.93 mol, 2.50 eq.) and 1,2-dibromoethane (152.0 mL, 1.76 mol, 1.50 eq.) were added to a stirred solution of methyl 3,4-dihydroxybenzoate (100B) (197.0 g, 1.17 mol, 1.0 eq.) in DMF (2.96 L). The reaction mixture was heated to 90° C. and stirred for 25 h. The progress of the reaction monitored by TLC (TLC analysis 60% Ethyl acetate in n-heptane). The reaction was cooled to RT then DMW (7.50 L) was added then extracted with EtOAc (2×3.50 L). The combined organic extract was washed with DMW (2×3.5 L) and brine (3.5 L), dried over sodium sulfate and concentrated under vacuum to obtain intermediate 100C (214.0 g, 94.10%) as a light brown oil. $^1$H NMR (300 MHz, CDCl$_3$): δ 7.63-7.51 ppm (m, 2H), 6.89 ppm (d, J=9.0 Hz, 1H), 4.35-4.24 ppm (m, 4H), 3.88 ppm (s, 3H).

Step C: Methyl 7-nitro-2,3-dihydrobenzo[b][1,4]dioxine-6-carboxylate (Intermediate 100D)

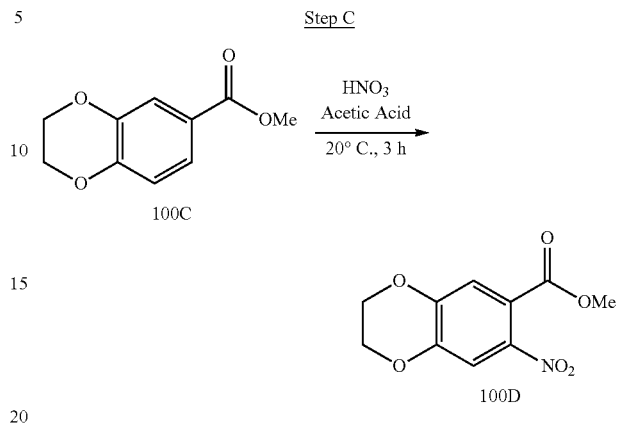

Conc. HNO$_3$ (832.0 mL, 14.50 mol, 17.0 eq.) was added slowly to a stirred solution of methyl 2,3-dihydrobenzo[b][1,4]dioxine-6-carboxylate (100C) (214.0 g, 1.10 mol, 1.0 eq.) in acetic acid (832.0 mL, 14.50 mol, 13.2 equiv.) at below 20° C. The reaction mixture was stirred at room temperature for 2 h while monitoring the progress of the reaction by TLC (Eluent: 60% Ethyl acetate in n-heptane). The reaction mixture was poured into ice-water (5.0 L) with vigorous stirring. The precipitated solid was collected by filtration, washed with DMW (1100 mL) and dried to obtain the intermediate 100D (261 g, 99.0%) as a light yellow solid. $^1$H NMR (300 MHz, DMSO-d6): δ 7.65 ppm (s, 1H), 7.30 ppm (s, 1H), 4.47-4.34 ppm (m, 1H), 4.39 ppm (s, 4H), 3.80 ppm (s, 3H).

Step D: Methyl 7-amino-2,3-dihydrobenzo[b][1,4]dioxine-6-carboxylate (Intermediate 100E)

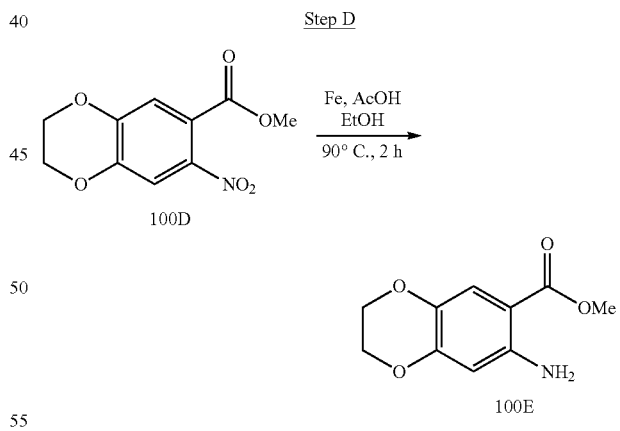

A mixture of methyl-7-nitro-2,3-dihydrobenzo[b][1,4]dioxine-6-carboxylate (100D) (260 g, 1.09 mol, 1.0 eq.), iron dust (217.0 g, 2.72 mol, 2.5 eq.; mesh size of 300-400) in ethanol (1.69 L, 6.50 vol. eq.), water (585 mL) and acetic acid (1.69 L) was heated to 80° C. and stirred at this temperature for 45 min. The progress of the reaction was monitored by TLC (eluent: 60% Ethyl acetate in n-heptane). The reaction mixture was cooled to RT and filtered through a celite bed and bed was washed with ethyl acetate (500 mL). Water (5.0 L) was added to the filtrate and mixed. The aqueous layer was separated and back extracted with ethyl acetate (3×2.0 L). The combined organic extract was washed with sat. sodium bicarbonate (3×3.0 L) and brine (5.0 L), then dried over sodium sulfate and filtered. The filtrate was concentrated under vacuum to obtain intermediate 100E (226 g, 99.40%) as a light brown solid. $^1$H NMR (300 MHz, DMSO-d6): δ 7.14 ppm (s, 1H), 6.27 ppm (s, 2H), 6.24 ppm (s, 1H), 4.28-4.19 ppm (m, 2H), 4.16-4.06 ppm (m, 2H), 3.73 ppm (s, 3H).

Step E: 7-Amino-2,3-dihydrobenzo[b][1,4]dioxine-6-carboxylic acid (Intermediate 100)

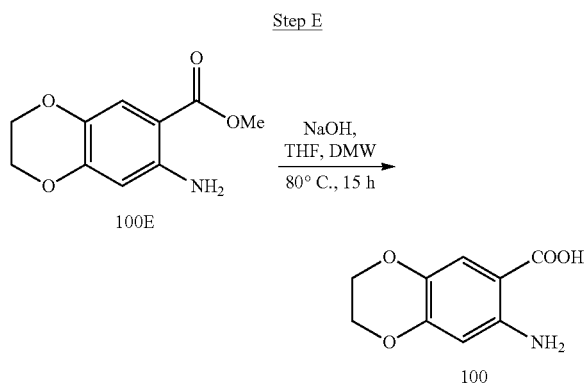

To a stirred solution of methyl-7-amino-2,3-dihydrobenzo[b][1,4]dioxine-6-carboxylate (100E) (225.0 g, 1.08 mol, 1.0 eq.) in THF (1.58 mL) was added NaOH solution (237.0 g, 5.92 mol, 5.50 eq.) in water (1.58 mL.) and the reaction mixture was heated to 80° C. and stirred for 15 h. The progress of the reaction was monitored by TLC (10% MeOH in DCM) to ensure the completion of the reaction. The reaction mixture was cooled to RT and the THF was evaporated under reduced pressure. Subsequently, cooled DMW (1500 mL) was added to the residue and the pH was adjusted to ~6.0 using 5N HCl. The precipitated solid was collected by filtration, washed with DMW (300 mL) and dried to afford intermediate 100 (152.50 g, 72.5%) as a light yellow solid. $^1$H NMR (300 MHz, DMSO): δ 8.17 ppm (s, 2H), 7.13 ppm (s, 1H), 6.20 ppm (s, 1H), 4.27-4.17 ppm (m, 2H), 4.17-4.02 ppm (m, 2H).

Step 7: Synthesis of 2-(4-bromo-2-(methylsulfonyl)phenyl)-7,8-dihydro-4H-[1,4]dioxino [2',3':4,5]benzo[1,2-d][1,3]oxazin-4-one (Intermediate 108)

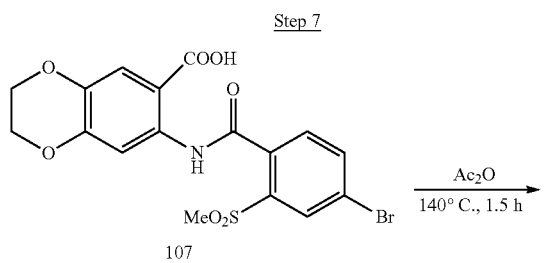

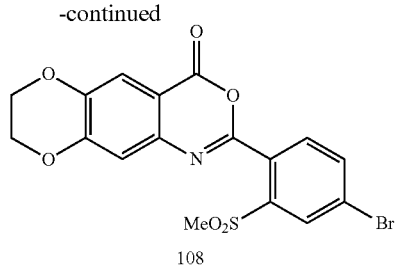

A solution of 7-(4-bromo-2-(methylsulfonyl)benzamido)-2,3-dihydrobenzo[b][1,4]dioxine-6-carboxylic acid (107) (120.0 g, 263.0 mmol, 1.0 eq.) in acetic anhydride (960 mL) was heated to 140° C. and stirred for 1.5 h. The progress of the reaction was monitored by TLC (50% EtOAc in n-hexane) to ensure completion of the reaction. About 70% solvent was removed by vacuum distillation. The remaining residue was cooled to RT then DMW (1000 mL) was added and the mixture was stirred for 40 min. The precipitated solid was collected by filtration, washed with DMW (1000 mL) and dried to intermediate 108 (85.4 g, 74.1%) as an off white solid. $^1$H NMR (300 MHz, DMSO-d$_6$): δ 8.29-8.12 ppm (m, 2H), 7.91 ppm (d, J=8.2 Hz, 1H), 7.59 ppm (s, 1H), 7.26 ppm (s, 1H), 4.55-4.32 ppm (m, 4H), 3.57 ppm (s, 3H). MS(ESI): m/z 439.6 (M+1).

Step 8: Synthesis of 2-(2-(methylsulfonyl)-4-vinylphenyl)-7,8-dihydro-4H-[1,4]dioxino[2',3':4,5]benzo[1,2-d][1,3]oxazin-4-one (Intermediate 109)

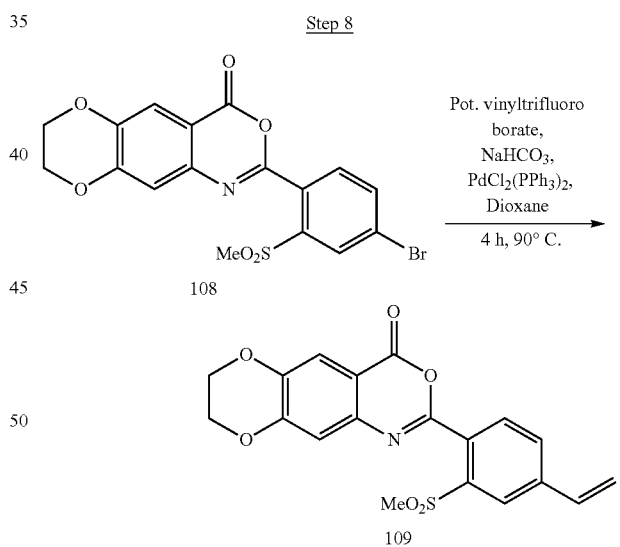

A solution of 2-(4-bromo-2-(methylsulfonyl)phenyl)-7,8-dihydro-4H-[1,4]dioxino[2',3':4,5]benzo[1,2-d][1,3]oxazin-4-one (108) (84.0 g, 192.0 mmol, 1.0 eq.) in 1,4-dioxane (1.68 L) was degassed three times by applying alternating vacuum and nitrogen refill to remove oxygen. Sodium bicarbonate (56.40 g, 671.0 mmol, 3.5 eq.), potassium vinyltrifluoro borate (64.20 g, 479.0 mmol, 2.5 eq.), tri(o-tolyl)-phosphine (14.60 g, 47.90 mmol, 0.25 eq.) and Pd(OAc)$_2$ (1.51 g, 6.71 mmol, 0.035 eq.) were added under nitrogen and the reaction flask was degassed two additional times with alternating vacuum and nitrogen refill. The reaction mixture was heated at 70° C. and stirred for 3.5 h. The progress of the reaction was monitored by TLC (40% EtOAc in n-hexane) to ensure completion of the reaction. The reaction mixture was cooled to room temperature, quenched with 1N HCl (1000 mL) and filtered through a hyflo pad. The solvent was evaporated under reduced pressure and DMW (2.5 L) was added to the residue. The product was extracted with ethyl acetate (3×2 L) and the combined EtOAc extract was washed with brine (2.5 L), dried over sodium sulfate, filtered and concentrated to provide the crude product. The crude product was stirred in diethyl ether (150 mL) and filtered to afford intermediate 109 (72.0 g, 97.50%) as a light yellow solid. $^1$H NMR (300 MHz, DMSO-$d_6$): δ 8.19-8.10 ppm (m, 1H), 8.06-8.00 ppm (m, 1H), 7.93 ppm (dd, J=7.9, 3.5 Hz, 1H), 7.58 ppm (s, 1H), 7.24 ppm (s, 1H), 6.96 ppm (dd, J=17.7, 11.0 Hz, 1H), 6.10 ppm (t, J=17.7 Hz, 1H), 5.56 ppm (d, J=11.0 Hz, 1H), 4.55-4.26 ppm (m, 4H), 3.56-3.46 ppm (m, 3H).

Step 9: Synthesis of 3-(methylsulfonyl)-4-(4-oxo-7,8-dihydro-4H-[1,4]dioxino[2',3':4,5]benzo[1,2-d][1,3]oxazin-2-yl)benzaldehyde (Intermediate 110)

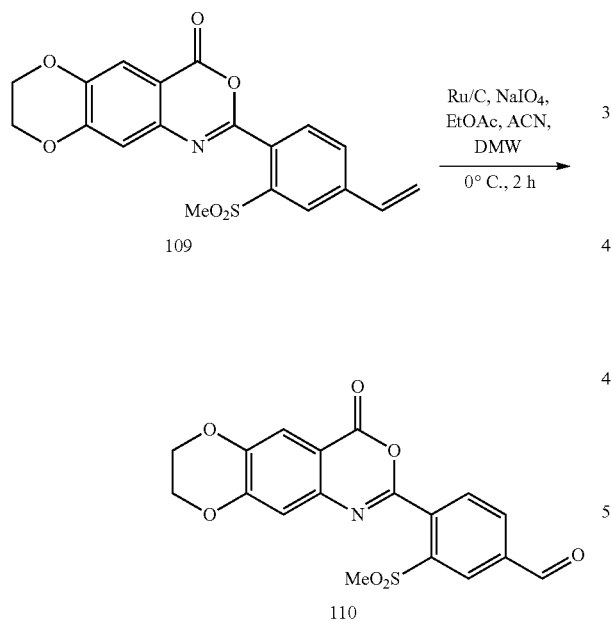

Ruthenium on carbon (10%) (5.66 g, 5.60 mmol, 0.03 eq.) was added to a solution of 2-(2-(methylsulfonyl)-4-vinylphenyl)-7,8-dihydro-4H-[1,4]dioxino[2',3':4,5]benzo[1,2-d][1,3]oxazin-4-one (109) (72.0 g, 187.0 mmol, 1.0 eq.) in acetonitrile (1.44 L.), EtOAc (1.44 L) and DMW (1.08 L) at RT. Sodium metaperiodate (130.0 g, 607.0 mmol, 3.25 eq.) was added at 0° C. The reaction mixture was stirred at 0° C. for 3.0 h. The progress of the reaction was monitored by TLC (50% EtOAc in n-hexane). The reaction mixture was filtered through a celite bed. The solid was washed with ethyl acetate (4×1.5 L). The filtrate was washed with water (3.0 L) and aqueous layer was back-extracted with ethyl acetate (800 mL). The combined organic extract was washed with brine (2.0 L), dried over sodium sulfate and filtered. The filtrate was concentrated under vacuum to obtain the crude product 110 (65.0, 95.30%) as a brown solid. The crude material of intermediate 110 was used directly in the following step 10.

Step 10: Synthesis of 2-(4-(hydroxymethyl)-2-(methylsulfonyl)phenyl)-7,8-dihydro-4H-[1,4]dioxino[2',3':4,5]benzo[1,2-d][1,3]oxazin-4-one (Compound 1.001)

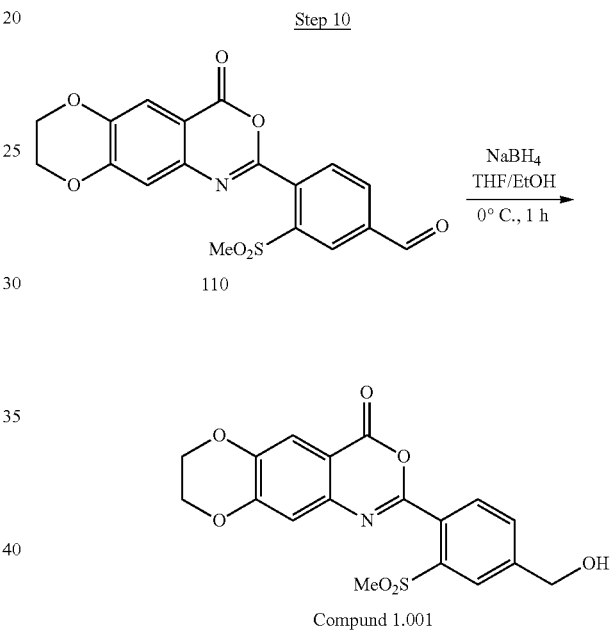

Sodium borohydride (8.0 g, 1.0 eq.) was added slowly to a stirred solution of 3-(methylsulfonyl)-4-(4-oxo-7,8-dihydro-4H-[1,4]dioxino[2',3':4,5]benzo[1,2-d][1,3]oxazin-2-yl)benzaldehyde (110) (82.0 g, 212.0 mmol, 1.0 eq.) in THF (1.23 mL) and ethanol (1.23 L) at 0° C., over the period of 1.0 h. The reaction mixture was stirred at 0° C. for 2h. The progress of the reaction was monitored by TLC (70% EtOAc in n-hexane) to ensure completion of the reaction. The reaction mixture was quenched with saturated solution of ammonium chloride (100 mL) and the product was extracted with ethyl acetate (3×1500 mL). The combined organic extract was washed with brine (500 mL), dried over sodium sulfate and concentrated under vacuum to obtain the crude product. The crude product was purified by column chromatography on silica gel (230-400 mesh size) using a gradient solvent (20-40% [(10% MeOH in EtOAc)] in n-hexane) to afford Compound 1.001 (15.50 g, 18.80%) as an off white solid. $^1$H NMR (300 MHz, DMSO-$d_6$): δ 8.08 ppm (d, J=1.5 Hz, 1H), 7.91 ppm (d, J=7.9 Hz, 1H), 7.83 ppm (dd, J=7.9, 1.6 Hz, 1H), 7.58 ppm (s, 1H), 7.24 ppm (s, 1H), 5.64 ppm (t, J=5.7 Hz, 1H), 4.70 ppm (d, J=5.7 Hz, 2H), 4.47-4.35 ppm (m, 4H), 3.50 ppm (s, 3H).

Example 2

2-(5-(Hydroxymethyl)-2-(methylsulfonyl)phenyl)-7,8-dihydro-4H-[1,4]dioxino[2',3':4,5]benzo[1,2-d][1,3]oxazin-4-one (compound 1.002)

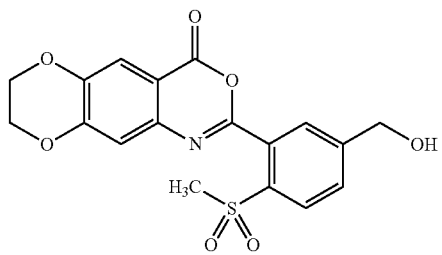 [SMILES: CS(=O)(=O)c1ccc(CO)cc1-c1nc2cc3c(cc2c(=O)o1)OCCO3]

Figure 2:
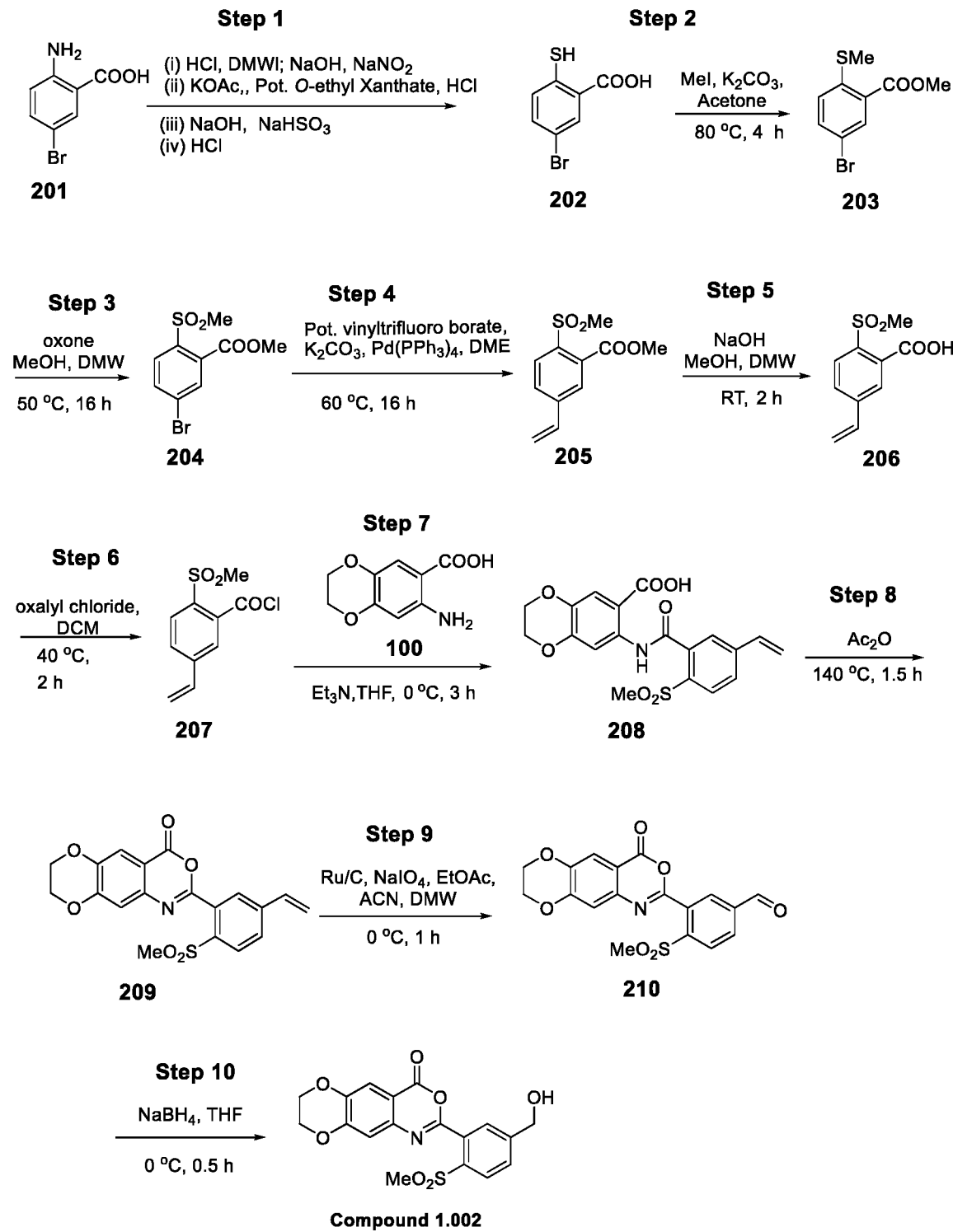
FIG. 2 shows a scheme for preparing Compound 1.002.

The synthesis of compound 1.002 is shown in FIG. 2. The synthesis of the intermediate 100 is illustrated in FIG. 3.

Step 1: 5-Bromo-2-mercaptobenzoic acid (Intermediate 202)

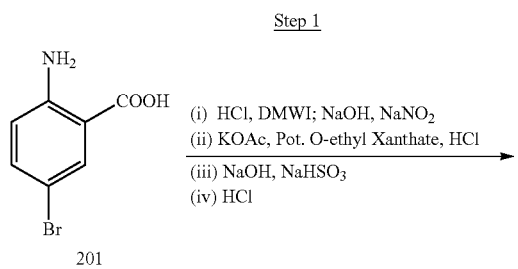

A mixture of concentrated HCl (28.0 mL) and chilled water (34 mL) was added dropwise to a stirred solution of 2-amino-5-bromobenzoic acid (201) (20.0 g, 92.6 mmol, 1.0 eq.), NaOH (3.70 g, 92.6 mmol, 1.0 eq.), and sodium nitrite (6.39 g, 92.6 mmol, 1.0 eq.) in DMW (400.0 mL) by maintaining the internal temperature 3-6° C. The reaction mixture was stirred at 0° C. for 30 min, and then neutralized with potassium acetate (30.0 g, 306.0 mmol, 3.3 eq.). This solution was added to a solution of potassium O-ethyl xanthate (44.6 g, 278.0 mmol, 3.0 eq.) in DMW (223 mL) which had preheated to 90° C. The mixture was stirred at the same temperature for 30 min, cooled to 0° C., and acidified with conc. HCl (100 mL). The reaction mixture was basified with 10% NaOH (200 ml), and heated to 85° C. for 2 h. To this mixture was added portion wise NaHSO₃ (9.81 g, 92.6 mmol), and the mixture was heated to 85° C. for 10 min. The mixture was filtered, cooled to 0° C., and acidified with conc. HCl (100 mL). The precipitate was collected by filtration and washed with H₂O and then n-hexane to get intermediate 202 (20.2 g, 93.6%) as a pale brown solid. MS (ESI): m/z 230.8 (M−1).

Step 2: Methyl 5-bromo-2-(methylthio)benzoate (Intermediate 203)

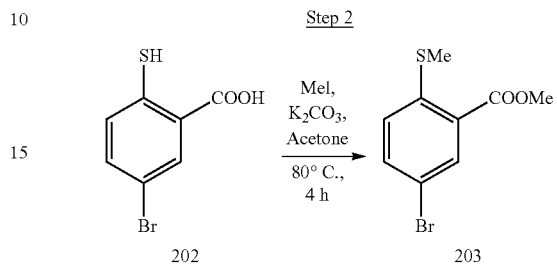

Potassium carbonate (83.0 g, 601 mmol, 7.0 eq.) and ethyl iodide (21.4 mL, 343 mmol, 4.0 eq.) were added 0° C. to a stirred solution of 5-bromo-2-mercaptobenzoic acid (202) (20 g, 85.8 mmol, 1 eq.) in DMF (600 mL) at RT. The reaction mixture was stirred at 80° C. for 4 h. The progress of the reaction was monitored by TLC (10% EtOAc in n-hexane) to ensure the completion of the reaction. DMW (500 mL) was added and the product was extracted with ethyl acetate (3×500 mL). The combined EtOAc extract was washed with brine (300 mL), dried over sodium sulfate, filtered and filtrate was concentrated under vacuum to get the crude compound. The crude product was purified by column chromatography on silica gel (230-400 mesh size) and gradient solvent (0-5% EtOAc in n-hexane) to afford intermediate 203 (20 g, 89.3%) as an off-white solid.

Step 3: Methyl 5-bromo-2-(methylsulfonyl)benzoate (Intermediate 204)

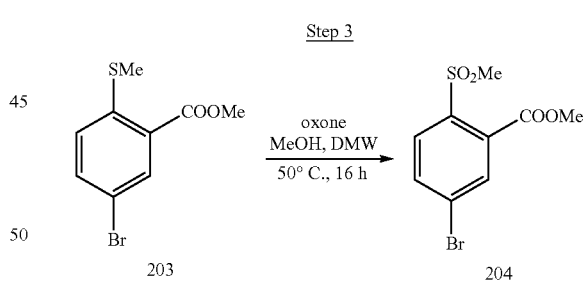

A solution of oxone (40.8 g, 268 mmol, 5.0 eq.) in DMW (280 mL) was added to stirred a solution of methyl 5-bromo-2-(methylthio)benzoate (203) (14.0 g, 53.6 mmol, 1.0 eq.) in methanol (350 mL) at 0° C. The reaction mixture was stirred at 50° C. for 16 h. The progress of the reaction was monitored by TLC (30% EtOAc in n-hexane) to ensure completion of the reaction. The product was extracted with EtOAc (4×500 mL). The combined organic extract was washed with brine (2×300 mL), dried over sodium sulfate and concentrated under vacuum to get crude. The crude product was purified by column chromatography on silica gel (230-400 mesh size) and gradient solvent (5-20% EtOAc in n-hexane) to afford intermediate 204 (13.2 g, 84.0%) as an off-white solid. ¹H NMR (300 MHz, DMSO): δ 8.08-7.98 ppm (m, 2H), 7.93 ppm (dd, J=7.9, 0.9 Hz, 1H), 3.87 ppm (s, 3H), 3.44-3.35 ppm (m, 3H). MS (ESI): m/z 292.8 (M−1).

Step 4: Methyl 2-(methylsulfonyl)-5-vinylbenzoate (Intermediate 205)

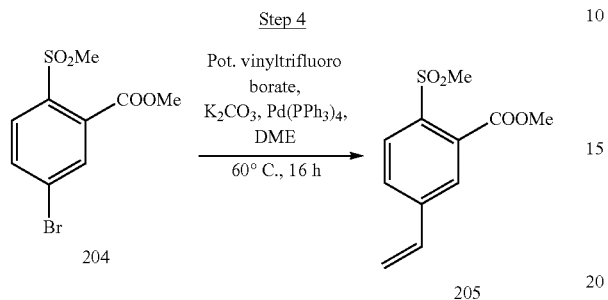

A solution of methyl 5-bromo-2-(methylsulfonyl)benzoate (204) (5.0 g, 17.1 mmol, 1.0 eq.) in DME (100.0 mL, 20 vol. equiv.) was degassed three times with alternating vacuum and nitrogen refill was degassed twice by alternate vacuum and nitrogen. Potassium carbonate (4.71 g, 34.1 mmol, 2.0 eq.), potassium vinyltrifluoro borate (4.57 g, 34.1 mmol, 2.0 eq.) and Pd(PPh$_3$)$_4$ (591 mg, 512 µmol, 0.03 eq.) were added under nitrogen and the reaction flask was degassed additional two times with alternating vacuum and nitrogen refill. The reaction mixture was heated at 80° C. and stirred for 4 h (N$_2$ was removed when temperature raised to 40-45° C.). The progress of the reaction was monitored by TLC (30% EtOAc in n-hexane) to ensure completion of the reaction. The reaction mixture was cooled to room temperature and filtered through a hyflo pad. DMW (300 mL) was added to the filtrate and the product was extracted with ethyl acetate (2×100 mL). The combined organic extract was washed with brine (2×100 mL), dried over sodium sulfate, filtered and concentrated to provide the crude product. The crude product was purified by column chromatography on silica gel (230-400 mesh size) using a gradient solvent (5-20% EtOAc in n-hexane) as eluent to afford intermediate 205 (3.36 g, 82.0%) as a light yellow gum.

Step 5: 2-(Methylsulfonyl)-5-vinylbenzoic acid (Intermediate 206)

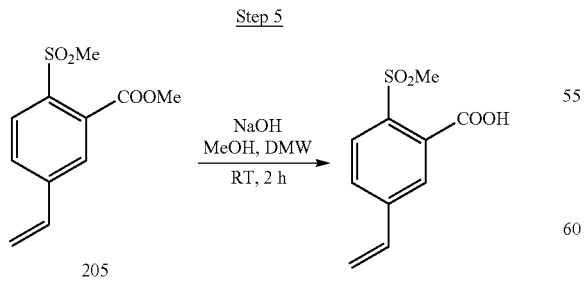

A solution of NaOH (3.92 g, 97.9 mmol, 7.0 eq.) in water (67.2 mL) was added to the stirred solution of methyl 2-(methylsulfonyl)-5-vinylbenzoate (205) (3.36 g, 14.0 mmol, 1.0 equiv) in methanol (67.2 mL). The reaction mixture was stirred at 60° C. for 2 h. The progress of the reaction was monitored by TLC (70% EtOH in n-hexane) to ensure completion of the reaction. Reaction mixture was cooled to RT, the pH was adjusted to ~6 using 3N HCl and aqueous layer was extracted with ethyl acetate (4×500 mL). The combined organic extract was washed with brine, dried over sodium sulfate, filtered and filtrate was concentrated under vacuum to get the desired intermediate 206 (1.48 g, 46.8%) as an off-white solid. $^1$H NMR (300 MHz, DMSO): δ 7.93 ppm (t, J=7.6 Hz, 1H), 7.88-7.78 ppm (m, 2H), 6.87 ppm (dd, J=17.7, 11.0 Hz, 1H), 6.13 ppm (d, J=17.6 Hz, 1H), 5.53 ppm (d, J=10.9 Hz, 1H), 3.37 ppm (s, 3H). MS (ESI): m/z 224.95 (M−1).

Step 6: 2-(Methylsulfonyl)-5-vinylbenzoyl chloride (Intermediate 207)

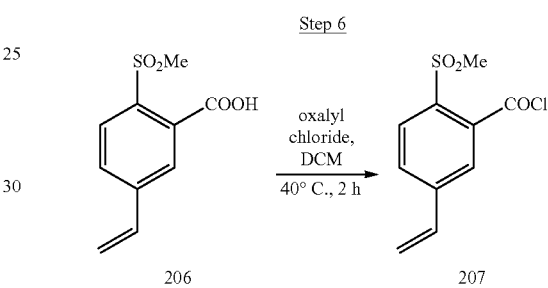

Oxalyl chloride (2.66 mL, 30.9 mmol, 5.0 eq.) was added to stirred a solution of 2-(methylsulfonyl)-5-vinylbenzoic acid (206) (1.4 g, 6.19 mmol, 1.0 eq.) in DCM (70 mL) followed by the addition of 2-drops of DMF at RT. The reaction mixture was refluxed for 2 h. The progress of the reaction was monitored by TLC (50% EtOAc in n-hexane) to ensure the completion of the reaction. The solvent was removed under vacuum to get the desired product as of intermediate 207 (540 mg, 83.2%). The rude material of intermediate 207 was used directly in the following step 7.

Step 7: 7-(2-(Methylsulfonyl)-5-vinylbenzamido)-2,3-dihydrobenzo[b][1,4]dioxine-6-carboxylic acid (Intermediate 208)

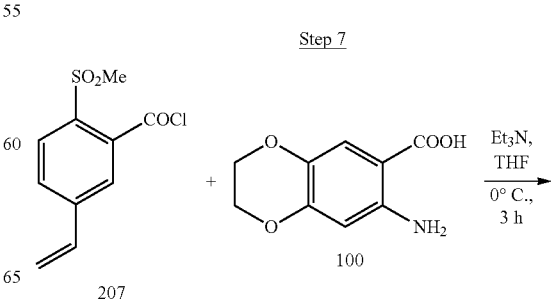

43

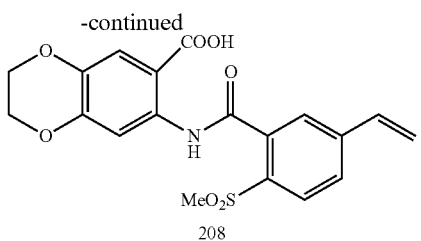
208

Triethylamine (1.93 mL, 13.8 mmol, 3.0 eq.) and a solution of 2-(methylsulfonyl)-5-vinylbenzoyl chloride (207) (1.35 mg, 5.53 mmol, 1.2 eq.) in THF (36 mL) was added to stirred a solution of 7-amino-2,3-dihydrobenzo[b][1,4]dioxine-6-carboxylic acid (100) (900 mg, 4.61 mmol, 1.0 eq.) in THF (36.0 mL) at 0° C. The reaction mixture was stirred at same temperature for 10 min and then at RT for 1.5 h. The progress of the reaction was monitored by TLC (20% EtOAc in n-hexane) to ensure the completion of the reaction. The solvent was removed under vacuum. DMW was added to the residue and the product was extracted with EtOAc (9×200 mL). The combined EtOAc extract was washed with brine (200 mL), dried over sodium sulfate and concentrated under vacuum to afford intermediate 208 (1.6 g, 86.0%) as a brown solid. MS(ESI): m/z 404.10 (M+1), m/z 401.90 (M−1).

Intermediate 100, 7-amino-2,3-dihydrobenzo[b][1,4]dioxine-6-carboxylic acid, was synthesized via steps A-E as described herein.

Step A: Methyl 3,4-dihydroxybenzoate (Intermediate 100B)

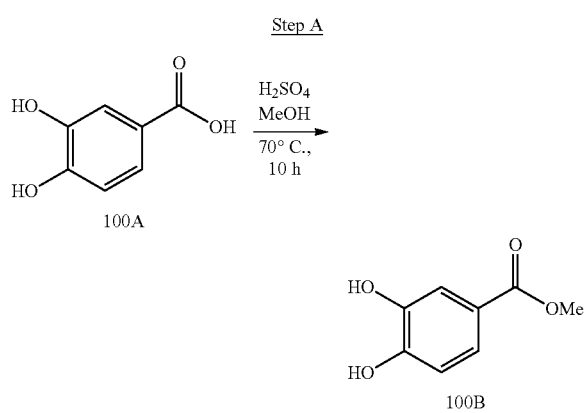

To a stirred solution of 3,4-dihydroxybenzoic acid (100A) (97%, 10.0 g, 62.9 mmol, 1.0 eq.) in MeOH (500 mL) was added sulfuric acid (96%, 7.0 mL, 126.0 mmol, 2.0 eq.) at RT. The reaction mixture was refluxed for overnight. TLC was checked to ensure the completion of reaction. The solvent was removed under vacuum and then water was added (500 mL). The aqueous layer was extracted with EtOAc (3×100 mL). The combined organic layers were washed with sat. NaHCO$_3$ solution (250 mL), brine (250 mL), dried over sodium sulfate and concentrated under vacuum to get the desired intermediate 100B (8.72 g, 82.4%) as an off-white solid. $^1$H NMR (300 MHz, DMSO-d6): δ 9.81 ppm (d, J=131.1 Hz, 2H), 7.41-7.19 ppm (m, 2H), 6.81 ppm (d, J=8.2 Hz, 1H), 3.77 ppm (s, 3H).

44

Step B: Methyl 2,3-dihydrobenzo[b][1,4]dioxine-6-carboxylate (Intermediate 100C)

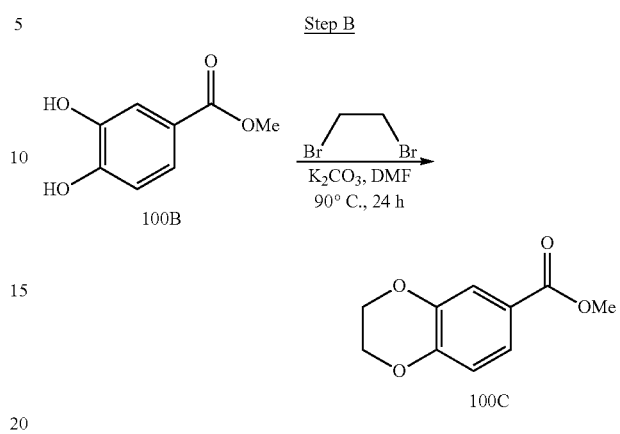

To a stirred solution of methyl 3,4-dihydroxybenzoate (100B) (10.0 g, 59.5 mmol, 1.0 eq.) in acetone (200.0 mL) was added potassium carbonate (20.5 g, 149 mmol, 2.50 eq.) followed by the addition of 1,2-dibromoethane (7.72 mL, 89.2 mmol, 1.50 eq.) and the reaction mixture was refluxed for overnight. TLC was checked to ensure the completion of reaction. The solvent was removed under vacuum and then water was added. The aqueous layer was neutralized with 1N HCl and then extracted with EtOAc (2×250 mL). The combined organic extract was washed with brine (500 mL), dried over sodium sulfate and concentrated under vacuum. The crude was purified by combiflash using ethyl acetate in n-hexane (0 to 10%) to get the desired intermediate 100C (9.0 g, 77.9%) as a colourless oil. $^1$H NMR (300 MHz, CDCl$_3$): δ 7.54-7.42 ppm (m, 2H), 6.85-6.75 ppm (m, 1H), 4.27-4.14 ppm (m, 4H), 3.79 ppm (s, 3H).

Step C: Methyl 7-nitro-2,3-dihydrobenzo[b][1,4]dioxine-6-carboxylate (Intermediate 100D)

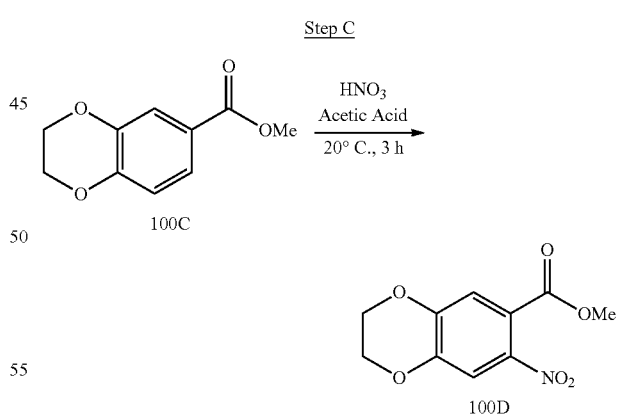

To a stirred solution of methyl 2,3-dihydrobenzo[b][1,4]dioxine-6-carboxylate 100C (9.0 g, 46.3 mmol, 1.0 eq.) in acetic acid (35.0 mL, 612 mmol, 13.2 eq.) was added dropwise conc. HNO$_3$ (47.0 mL, 788 mmol, 17.0 equiv.) at below 20° C. and the reaction mixture was allowed to stirred at room temperature for 2 h. TLC was checked to ensure the completion of reaction. The reaction mixture was poured into ice-water with vigorous stirring and the aqueous layer was extracted with EtOAc (3×500 mL). The combined organic extract was washed with NaHCO₃, brine, dried over sodium sulfate and concentrated under vacuum to get the desired product as of intermediate 100D (9.7 g, 87.5%) as a pale yellow solid. ¹H NMR (300 MHz, DMSO-d6): δ 7.65 ppm (s, 1H), 7.30 ppm (s, 1H), 4.47-4.34 ppm (m, 1H), 4.39 ppm (s, 4H), 3.80 ppm (s, 3H).

Step D: Methyl 7-amino-2,3-dihydrobenzo[b][1,4]dioxine-6-carboxylate (Intermediate 100E)

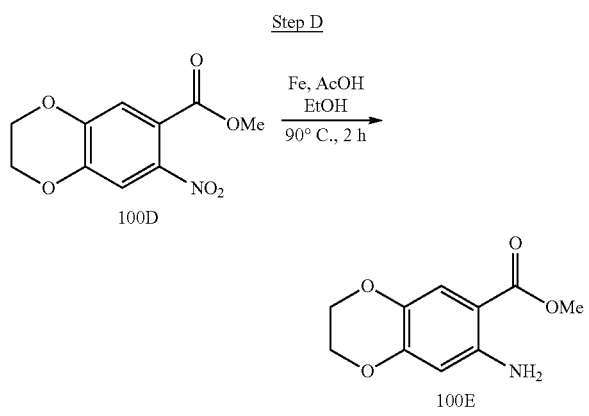

A mixture of methyl-7-nitro-2,3-dihydrobenzo[b][1,4]dioxine-6-carboxylate (100D) (25.0 g, 105.0 mmol, 1.0 eq.), iron (20.4 g, 366.0 mmol, 3.5 eq.), ethanol (625 mL), water (163 mL) and acetic acid (500 mL) was stirred at 70° C. for 45 min. TLC was checked to ensure the completion of reaction. The reaction mixture was cooled to RT and filtered through hyflo pad. The filtrate was diluted with water (1000 mL) and aqueous layer was extracted with ethyl acetate (3×700 mL). The combined organic extract was washed with sat. sodium bicarbonate (2×1000 mL), brine (1000 mL), dried over sodium sulfate and filtered. The filtrate was concentrated under vacuum to afford titled compound as of intermediate 100E (21.8 g, 99.7%) as a brown solid. ¹H NMR (300 MHz, DMSO): δ 7.14 ppm (s, 1H), 6.25 ppm (d, J=7.6 Hz, 3H), 4.26 -4.19 ppm (m, 2H), 4.17-4.08 ppm (m, 2H), 3.73 ppm (s, 3H). MS (ESI): m/z 210.10 (M+1).

Step E: 7-Amino-2,3-dihydrobenzo[b][1,4]dioxine-6-carboxylic acid (Intermediate 100)

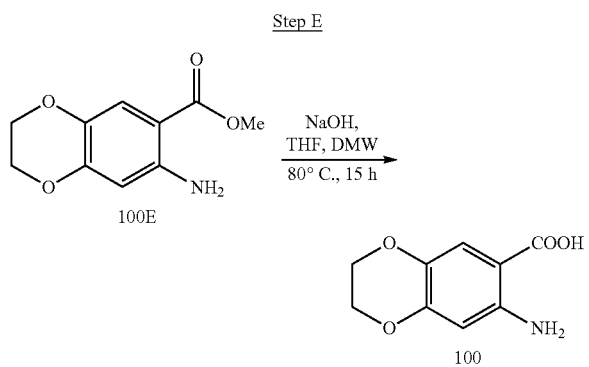

To a stirred solution of methyl-7-amino-2,3-dihydrobenzo[b][1,4]dioxine-6-carboxylate (100E) (22.0 g, 105 mmol, 1.0 eq.) in THF (440.0 mL) was added NaOH solution (23.1 g, 578 mmol, 5.5 eq.) in water (440.0 mL) and the reaction mixture was stirred at 80° C. for 20 h. The progress of the reaction was monitored by TLC (10% MeOH in DCM) to ensure the completion of the reaction. Reaction mixture was cooled to RT, the pH was adjusted to 6 using 3N HCl and aqueous layer was extracted with ethyl acetate (5×500 mL). The combined organic layers were washed with brine, dried over sodium sulfate, filtered and filtrate was concentrated under vacuum to get solid brown crude product. The crude was purified with n-hexane to get the desired intermediate 100 (18.6 g, 90.6%) as brown solid. ¹H NMR (300 MHz, DMSO): δ 8.27 ppm (s, 2H), 7.13 ppm (s, 1H), 6.20 ppm (s, 1H), 4.27-4.19 ppm (m, 2H), 4.18-4.08 ppm (m, 2H).

Step 8: 2-(2-(methylsulfonyl)-5-vinylphenyl)-7,8-dihydro-4H-[1,4]dioxino[2',3':4,5]benzo[1,2-d][1,3]oxazin-4-one (Intermediate 209)

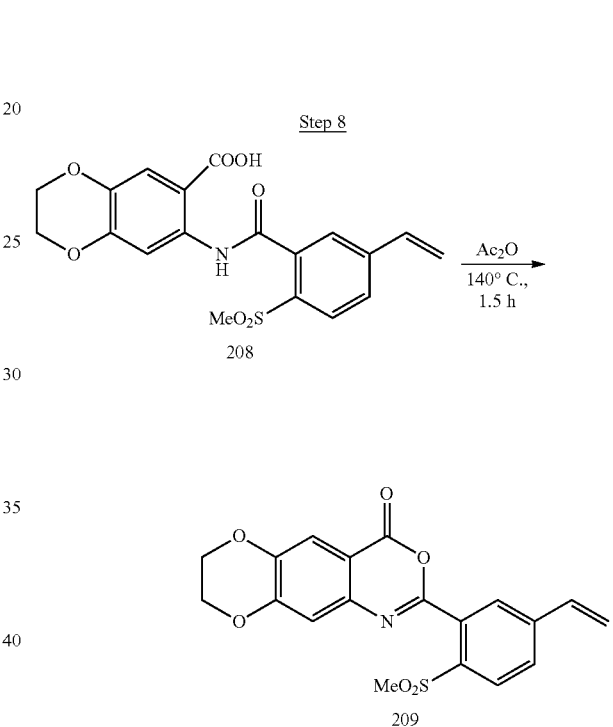

A solution of 7-(2-(methylsulfonyl)-5-vinylbenzamido)-2,3-dihydrobenzo[b][1,4]dioxine-6-carboxylic acid (208) (1.60 mg, 3.97 mmol, 1.0 eq.) in acetic anhydride (40 mL) was stirred at 140° C. for 1.5 h. The progress of the reaction was monitored by TLC (50% EtOH in n-hexane) to ensure completion of the reaction. The reaction mixture was cooled to RT then DMW (100 mL) was added. The product was extracted with EtOAc (4×200 mL). The combined EtOAc extract was washed with brine (2×200 mL), dried over sodium sulfate and concentrated under vacuum to get crude. The crude product was purified by column chromatography on silica gel (230-400 mesh size) and gradient solvent (20-50% EtOAc in n-hexane) to afford intermediate 209 (700 mg, 45.8%) as a yellow solid. ¹H NMR (300 MHz, CDCl3): δ 8.15 ppm (d, J=8.2 Hz, 1H), 7.90 ppm (d, J=1.7 Hz, 1H), 7.77-7.68 ppm (m, 2H), 7.16 ppm (s, 1H), 6.82 ppm (dd, J=17.5, 10.9 Hz, 1H), 6.01 ppm (d, J=17.5 Hz, 1H), 5.57 ppm (d, J=10.9 Hz, 1H), 4.40 ppm (dd, J=11.8, 5.3 Hz, 5H), 3.52 ppm (d, J=3.0 Hz, 3H). MS(ESI): m/z 385.80 (M+1).

Step 9: 3-(methylsulfonyl)-4-(4-oxo-7,8-dihydro-4H-[1,4]dioxino[2',3':4,5]benzo[1,2-d][1,3]oxazin-2-yl)benzaldehyde (Intermediate 210)

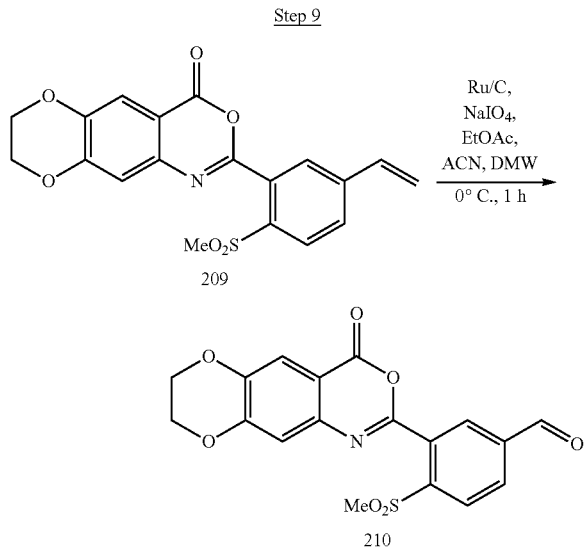

Ruthenium on carbon (10%) (50 mg, 0.049 mmol, 0.03 eq.) was added to a solution of 2-(2-(methylsulfonyl)-5-vinylphenyl)-7,8-dihydro-4H-[1,4]dioxino[2',3':4,5]benzo[1,2-d][1,3]oxazin-4-one (209) (0.630 g, 1.63 mmol, 1.0 eq.) in acetonitrile (12.6 mL), EtOAc (12.6 mL) and DMW (12.6 mL) at RT. Sodium metaperiodate (1.05 g, 4.9 mmol, 3.0 eq.) was added at 0° C. The reaction mixture was stirred at RT for 1 h. The progress of the reaction was monitored by TLC (30% EtOAc in n-hexane) to ensure completion of the reaction. The reaction mixture was filtered through celite bed. The filtrate was diluted with water (100 mL) and aqueous layer was extracted with ethyl acetate (3×200 mL). The combined organic extract was washed with sat. sodium bicarbonate, brine, dried over sodium sulphate and filtered. The filtrate was concentrated under vacuum to get crude intermediate 210. The crude product of intermediate 210 was used directly in the following step 10.

Step 10: 2-(4-(hydroxymethyl)-2-(methylsulfonyl)phenyl)-7,8-dihydro-4H-[1,4]dioxino[2',3':4,5]benzo[1,2-d][1,3]oxazin-4-one (Compound 1.002)

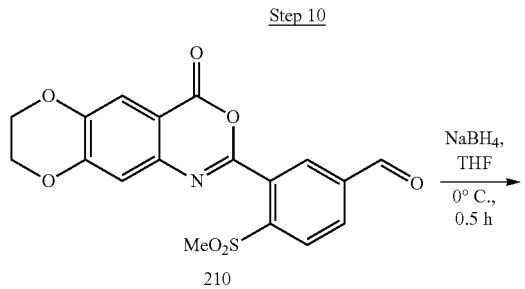

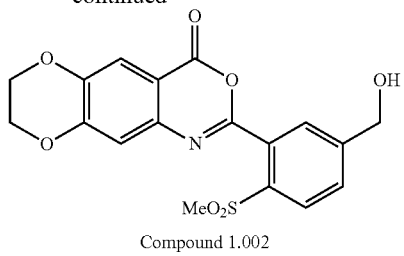

Compound 1.002

Sodium borohydride (9.77 mg, 0.258 mmol, 0.5 eq.) was added over the period of 1 h to a stirred solution of 4-(methylsulfonyl)-3-(4-oxo-7,8-dihydro-4H-[1,4]dioxino[2',3':4,5]benzo[1,2-d][1,3]oxazin-2-yl)benzaldehyde (210) (0.20 g, 0.52 mmol, 1.0 eq.) in THF (10.0 mL) at −10° C. The reaction mixture was stirred at 0° C. same temperature for 30 min. The progress of the reaction was monitored by TLC (70% EtOAc in n-hexane) to ensure completion of the reaction. The reaction mixture was quenched with saturated solution of ammonium chloride (50 mL) and the product was extracted with ethyl acetate (3×100 mL). The combined organic extract was washed with brine (500 mL), dried over sodium sulfate and concentrated under vacuum to obtain the crude product. The crude product was purified by column chromatography on silica gel (230-400 mesh size) using a gradient solvent (20-40% [(10% MeOH in EtOAc)] in n-hexane) to afford Compound 1.002(70 mg, 34.80%) as an off white solid. $^1$H NMR (300 MHz, DMSO): δ 8.07 ppm (d, J=8.2 Hz, 1H), 7.88 ppm (s, 1H), 7.79 ppm (d, J=8.5 Hz, 1H), 7.58 ppm (s, 1H), 7.24 ppm (s, 1H), 5.63 ppm (t, J=5.7 Hz, 1H), 4.69 ppm (d, J=5.6 Hz, 2H), 4.52-4.31 ppm (m, 4H), 3.48 ppm (s, 3H). MS (ESI): m/z 390.0 (M+1).

Example 3

In Vitro Activity Assays

Human Kallikrein Proteins: Recombinant human KLK5 expressed in HEK293 was obtained from SpeedBio (Gaithersburg, Md.). Recombinant proenzyme KLK-7 and recombinant proenzyme KLK-14 both expressed in mouse myeloma cells were from R&D Biosystems (Minneapolis, Minn.). Plasmin and thrombin were from Haematologic Technologies (Essex Junction, Vt.). Trypsin and Chymotrypsin were bought from Worthington Biochemical Corporation (Lakewood, N.J.) and plasma kallikrein was from Prospec (East Brunswick, N.J.). Neutrophil Elastase was obtained from Innovative Research (Peary Court, Mich.). Bovine recombinant enterokinase expressed in E. coli was bought from Sigma (St. Louis, Mich.). Matriptase expressed in E.coli was obtained from Enzo Life Sciences (Farmingdale, N.Y.). The control inhibitors Nafamostat mesylate was from Sigma (St. Louis, Mich.) and (2-(2-fluorophenyl)-5,6,7,8-tetrahydro-4H-benzo[4,5]thieno[2,3-d][1,3]oxazin-4-one was from Interbioscreen (Moscow, Russia).

Substrates: S-2288 (D-Ile-Pro-Arg-pNA), CS-PSA (MeO-Suc-Arg-Pro-Tyr-pNA), S-2266 (H-D-Val-Leu-Arg-pNA) and S-2288 (H-D-Ile-Pro-Arg-pNA) were bought from Diapharma (West Chester, Ohio). MeOSuccAla-Ala-Pro-Val-pNA was purchased from Sigma (St Louis, Mich.). The substrates were dissolved in water at 10 mM and were frozen in aliquots at −20° C.

Activation of KLK-7 and KLK-14: 150 μL 8 μM solution of the proenzymes of KLK-7 or KLK-14 in 50 mM Tris, 10 mM $CaCl_2$, 150 mM NaCl, 0.05%(w/v) Brij-35, pH 7.5 were mixed with 150 µL 10 µg/mL bovine enterokinase in the same buffer and incubated for 2 h for KLK-7 and 1 h for KLK-14 at 37° C. After the incubation period, activation was stopped by addition of 6 µL 0.5 M EDTA pH 8.0.

Assays: All assays were performed in 384 well polystyrene plates coated overnight with 0.1% Tween 20 at 4° C. The plates were then washed twice with 100 µL water and dried. For the determination of $IC_{50}$ values, the inhibitors were diluted in serial dilutions of 1:3 intervals into pure DMSO at 50 fold of the intended final concentrations in the assays. Usually eight inhibitor dilutions and one DMSO control were prepared. The substrates were diluted into water at 2.2-fold the final concentration in the assay mixture. The wells of the plate were filled with 50 µL of the enzyme diluted in 2×assay buffer (100 mM Tris, 200 mM NaCl, 0.2% PEG, 0.01% Tween, 2 mM EDTA, pH 8.0) at twofold the intended concentration. Then 5 uL DMSO, 2.2 uL inhibitor and 45 uL substrate were added to start the reaction. The assays were monitored at 37° C. in a multi well plate reader at a wavelength of 405 nm (Molecular Devices, San Jose, Calif.) for 1 h. The tool inhibitor, nafamostat, was used as a control for trypsin, thrombin, KLK-5 and KLK-14 at 10 uM maximal concentration and (2-(2-fluorophenyl)-5,6,7,8-tetrahydro-4H-benzo[4,5]thieno[2,3-d][1,3]oxazin-4-one for KLK-7 at 5 uM.

The table summarizes assay conditions for the individual enzymes:

| Enzyme | Enzyme Concentration (nM) | Substrate | Substrate Concentration (µM) |
| --- | --- | --- | --- |
| KLK-7 | 20 | CS-PSA | 500 |
| KLK-5 | 10 | S-2288 | 500 |
| KLK-14 | 5 | S-2288 | 500 |
| Plasma Kallikrein | 5 | S-2266 | 200 |
| trypsin | 0.1 | S-2288 | 500 |
| chymotrypsin | 0.2 | CS-PSA | 500 |
| plasmin | 1 | S-2288 | 500 |
| thrombin | 0.5 | S-2288 | 200 |
| matriptase | 0.015 U/µL | S-2288 | 200 |

Data analysis: The progress curves of substrate hydrolysis were analyzed by linear regression of the final 20 min of the reaction. Fit of the dose response of the resulting rates to the following equation yielded the $IC_{50}$:

$$\text{rate} = c + \frac{d - c}{1 + \exp(b * \log(x) - \log(IC50))}$$

with

1) $c$: the background rate at the highest inhibitor concentration;

2) $d$: the rate of the control reaction;

3) $IC_{50}$: the $IC_{50}$ of the inhibitor;

4) $x$: the inhibitor concentration; and

5) $b$: the slope.

Example 4

Protease Activity in Human Skin

Materials: The peptide substrates PS-01 (YRSR-pNA Tyr-Arg-Ser-Arg-pNA) (SEQ ID NO. 1) and PS-02 (Lys-His-Leu-Tyr-pNA) (SEQ ID NO. 2) were synthesized by Zamboni Chemical Solutions (Montreal, Canada). Human epidermis samples were obtained from Biopredic (Saint-Grégoire, France). The BCA protein assay kit was bought from VWR.

Preparation of skin extract: The epidermis was frozen and lyophilized. A sample of 15 mg lyophilized epidermis was immersed in 1 mL high salt buffer (100 mM Tris, 5 mM EDTA, 2M KCl, pH 8), frozen twice in dry ice and thawed. After incubation overnight at 4° C. and addition of six 2.4 mm metal beads, the sample was homogenized in a Bertin Precellys Homogenizer (Atkinson, N.H.) three times at 5000 Hz for 20 seconds each and cooled in between for 30 seconds. After centrifugation at maximal speed in a desktop minifuge, the protein concentration of the supernatant was determined by BCA assay (~0.5 mg/mL).

Inhibition of protease activity in skin extract: Stock solutions of 200, 66, 22 and 0 µM of the tested compound in DMSO were prepared. Substrate stocks of 1100 µM PS-01 and PS-02 were prepared by dissolving in water. The wells of a 384 well plate was filled with 50 µL 2×assay buffer (see above) and then 45 82 L substrate stock and 5 µL of the test compound were added. The reaction was started by addition of 10 µL skin extract for the substrate PS-02 and 5 µL for the substrate PS-01. The substrate hydrolysis was monitored in multi-well plate reader at 405 nm.

Example 5

Assay Results of Tested Compounds

Compounds 1.001 and 1.002 as well as a known compound 14 were tested according to assay protocols of Examples 3 and 4. The test results are listed in Table 2. Compound 14 is disclosed in WO 2015/112081 and has the formula:

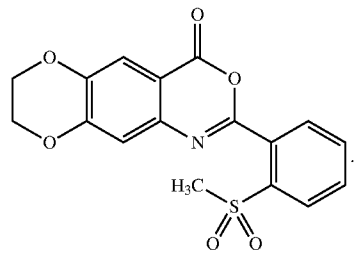 [SMILES: CS(=O)(=O)c1ccccc1-c1nc2cc3c(cc2c(=O)o1)OCCO3]

TABLE 2

Assay Results of Tested Compounds

| | Conc | Comp. 14 | Comp. 1.001 | Comp. 1.002 |
| --- | --- | --- | --- | --- |
| Recombinant KLK5 enzyme ($IC_{50}$) | | 0.24 µM | 0.21 µM | 1.57 µM |
| Recombinant KLK7 enzyme ($IC_{50}$) | | 0.13 µM | 0.34 µM | 0.22 µM |
| Rate in Skin Assay Substrate depletion rate constant | 1 µM | 0.14* 0.1* | 0.004* 0.02* | 0.009* 0.06* |
| | 3.3 µM | 0.08* | 0.04* | 0.05* |
| Initial rate of proteolytic activity | 1 µM | 0.13* | 0.04* | 0.1* |
| | 3.3 µM | 0.11* | 0.07* | 0.09* |

*Absorbance$_{405}$/min

Chromogenic substrate cleavage progressions of Compounds 1.001, 1.002, and 14 were tested according to human stratum corneum extract assay of Example 4 using KLK5 and KLK7 preferred chromogenic peptide substrates (PS-01 and PS-02). The proteolytic cleavage of KLK5 selective substrate in skin extract by Compounds 1.001, 1.002, and 14 are compared and shown in FIGS. 4A-4D. NSK refers to extract from skin freshly prepared; and OSK refers to extract from skin post freeze thaw.

As it can be seen from FIGS. 4A-4D (NSK), for compound 1.001, the rate (slope) of the initial linear part of curves appears to be lower than for other two compounds, indicating a higher inhibition of cleavage of substrate. The observed lower initial rate of proteolytic activity for compound 1.001 is also consistent with the observed lower intercept of the curves. As it can be seen from FIGS. 4A-4D (NSK), the rate of substrate cleavage slows down exponentially as substrate is depleted. The lower exponential rate constant for compound 1.001 indicates that compound 1.001 appears to have more potent inhibition of proteolytic activity.

In contrast to the results with purified recombinant KLK 5, based on three parameters (rate, substrate depletion and initial rate of proteolytic activity), compound 1.001 appears to be a more potent inhibitor of the proteolytic activity of skin extract, as compared to the known compound 14.

Example 6

Chromogenic Assay

Preparation of neonatal human epidermal keratinocyte lysate: Human epidermal keratinocytes pooled (HEK) were purchased form Invitrogen (Catalog #A13401). Cells were grown in commercial media EpiLife (ThermoFisher, Catalog #MEPI500CA) supplemented with commercial supplement S7 (ThermoFisher, Catalog #SO0175) in the absence of serum. Tissue culture was done at 37° C., in humidified chamber with 5% carbon dioxide. HEK Lysis buffer composition: 100 mM Tris-HCl, 150 mM NaCl, 1% triton, 5 mM EDTA, Final pH 7.6. After two passages the cells were lysed using HEK lysis buffer without added protease and phosphatase inhibitors and the protein concentration was determined using the bicinchoninic acid assay (BCA) (ThermoFisher, Catalog #23225).

Preparation of healthy human volunteer stratum corneum extract: Stratum corneum sheets were purchased from Biopredic (Catalog #STR0020). Extract preparation: stratum corneum lysate was prepared using Minute total protein extraction kit for Adipose tissues (InventBiotech, Catalog #AT-022) after homogenization per manufacturer's instructions. The overall protein concentration was determined with the BCA assay (ThermoFisher, Catalog #23225). The extracts were flash frozen and stored at −80° C. until used.

Concentration of KLK5 in the Stratum Corneum extract: The concentration of KLK5 in the Stratum Corneum extract was determined by 1) ELISA from Abcam (Catalog #ab131555); and 2) comparison of the rate of hydrolysis of the selective chromogenic substrate PS-01 (YRSR-pNA Tyr-Arg-Ser-Arg-pNA) with that of known concentrations of purified KLK5 (Speed Bio). Further, the concentration of KLK5 in an unknown sample was determined from the rate of hydrolysis of the selective substrate by interpolation from a linear plot of the rates of known samples.

Cleavage of macromolecular substrates by endogeneous and exogenous kallikrein 5: 10 ug of HEK lysate was incubated with equal volume of stratum corneum extract or protease in buffer at 37° C. for 1.5 h. The reactions were quenched by boiling for 5 min at 100° C. with loading buffer under reducing conditions (50 mM DTT). The proteins were separated by electrophoresis on bis-tris gels with an 4-12% acrylamide gradient which were run for 22 minutes at 200V. Following transfer of the proteins to PVDF membranes, non-specific binding was blocked using Intercept blocking buffer (Licor) for one hour at room temperature. The signals on the blots were normalized by GAPDH.

Conditions for detecting specific proteins are summarized below:

Desmoglein 1: the desmoglein antibody sc-137164 (Santa Cruz Biochemicals) was diluted 1/750 and incubated for 18 h at 40° C. After washing, secondary anti-mouse antibody (Licor) was added after dilution 1/20000 of the stock solution. The controls in absence of KLK5 were treated with protease/phosphatase inhibitor mix (Cell Signalling, #5872).

Desmocollin 1: The anti-Desmocollin 1 antibody (Abcam, 150382) was diluted 1:1000. The secondary antibody was diluted 1:15000. After washing, secondary anti-rabbit was added, after dilution 1:15000.

Filaggrin: The anti-filaggrin (LS-Bio, 1561) was diluted 1:400. The secondary antibody was diluted 1:10000.

Chromogenic Assay Results

Proteases: KLK5 (SpeedBioSystems); KLK7 (R&Dsystems) was activated with enterokinase (2 hours, 37° C.) prior to assay; Trypsin (Sigma Aldrich); Chymotrypsin (Sigma Aldrich); Factor Xa (Haematologic Technologies); Plasmin (Haematologic Technologies); KLK14 (R&Dsystems) was activated with enterokinase (1 hour, 37° C.) prior to assay; Thrombin (Haematologic Technologies); Neutrophil Elastase (Athens Research&Technology); and KLK1 (Prospec).

Compound 408: a product resulting from hydrolytic opening of the 4-quinazolinone moiety of Compound 1.001, represented by the formula:

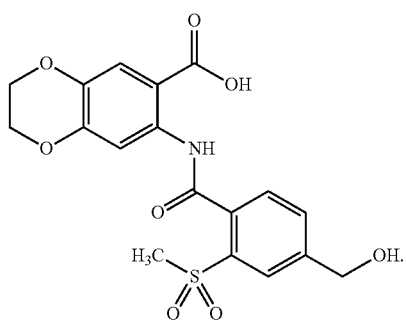 [SMILES: CS(=O)(=O)c1cc(CO)ccc1C(=O)Nc1cc2c(cc1C(=O)O)OCCO2]

The assay results are listed in Table 3.

TABLE 3

Chromogenic Assay Results of Compound 1.001 and Compound 408.

| Protease | | Subtrate | | | Comp. 1.001 | Comp. 408 |
| --- | --- | --- | --- | --- | --- | --- |
| name | conc. tested | name | conc. Tested | Highest conc. | IC$_{50}$ (μM) | IC$_{50}$ |
| KLK5 | 10 nM | S-2288 | 500 μM | 10 μM | 0.176 μM (n = 2); 0.188 μM (n = 2) | No inhibition |
| KLK7 | 20 nM | CS-PSA | 500 μM | 20 μM | 0.693 μM (n = 2); 0.647 μM (n = 2) | No inhibition |
| Trypsin | 0.1 nM | S-2288 | 500 μM | 50 μM | 1.664 μM (n = 2); 1.363 μM (n = 2); 2.204 μM (n = 2) | No inhibition |
| Chymotrypsin | 0.2 nM | CS-PSA | 500 μM | 50 μM | 0.249 μM (n = 2); 0.317 μM (n = 2) | No inhibition |
| Factor Xa | 0.5 nM | S-2288 | 500 μM | 20 μM | 3.217 μM (n = 2); 10.40 μM (n = 2); 3.935 μM (n = 2) | No inhibition |
| Plasmin | 1.0 nM | S-2288 | 500 μM | 50 μM | 3.357 μM (n = 2); 4.196 μM (n = 2) | No inhibition |
| KLK14 | 5 nM, 1 nM | S-2288 | 500 μM | 50 μM | 0.633 μM (5 nM)$^a$; 0.442 μM (1 nM)$^b$ | No inhibition |
| Thrombin | 0.5 nM | S-2288 | 500 μM | 100 μM | >10 μM (n = 2); >10 μM (n = 2); >10 μM (n = 2) | No inhibition |
| Neutrophil Elastase | 0.5 nM | Elastase substrate 1 | 200 μM | 100 μM | >50 μM (n = 2); >50 μM (n = 2) | >500 μM |
| KLK1 | 10 nM | S-2266 | 200 μM | 50 μM | No inhibition | No inhibition |

S-2288, S-2266 and CS-PSA were from Diapharma and dissolved in water at 10 mM solution; and Elastase substrate 1 was from Sigma and dissolved in water at 0.8 mM solution.
$^a$IC$_{50}$ at a concentration of 5 nM of KLK14; and $^b$IC$_{50}$ at a concentration of 1 nM of KLK14.

Conclusions: It can be concluded that compound 1.001 is an inhibitor of KLK5, KLK7 and Chymotrypsin. In contrast, compound 408 that lacks the 4-quinazolinone moiety (i.e., the pharmacophore of compound 1.001) is unable to inhibit proteases.

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Chemical moiety P-nitroanilide at the
      C-terminal residue

<400> SEQUENCE: 1

Tyr Arg Ser Arg
1

<210> SEQ ID NO 2
<211> LENGTH: 4
<212> TYPE: PRT
<213> ORGANISM: Artificial sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: Chemical moiety P-nitroanilide at the
      C-terminal residue
```

What is claimed is:

1. A compound represented by formula (I):

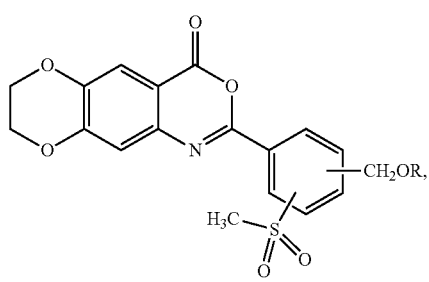

or a pharmaceutically acceptable complex thereof; wherein R is H or a member selected from the group consisting of —$R^1$ and —C(O)$R^{1a}$, wherein $R^1$ is $C_{1-12}$ alkyl, and $R^{1a}$ is H or $C_{1-12}$ alkyl.

2. The compound of claim 1, represented by formula (Ia):

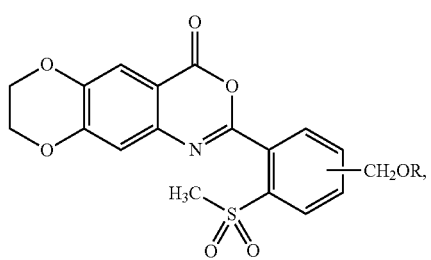

or a pharmaceutically acceptable complex thereof.

3. The compound of claim 1, represented by formula (Ib):

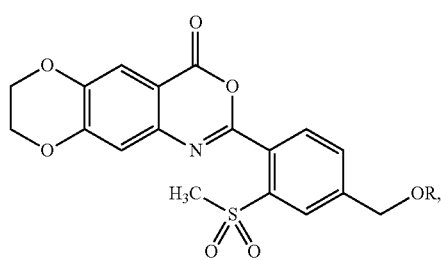 [SMILES: CS(=O)(=O)c1cc(CO)ccc1-c1nc2cc3c(cc2c(=O)o1)OCCO3]

or a pharmaceutically acceptable complex thereof.

4. The compound of claim 1, represented by formula (Ic):

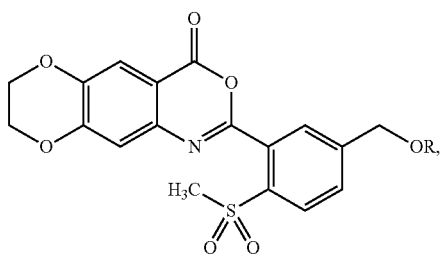 [SMILES: CS(=O)(=O)c1ccc(CO)cc1-c1nc2cc3c(cc2c(=O)o1)OCCO3]

or a pharmaceutically acceptable complex thereof.

5. The compound of claim 1, represented by the formula:

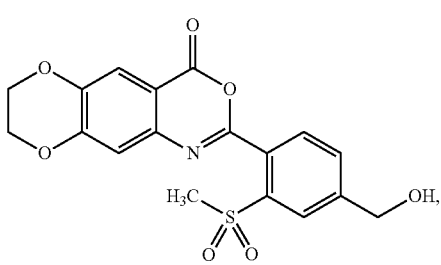 [SMILES: CS(=O)(=O)c1cc(CO)ccc1-c1nc2cc3c(cc2c(=O)o1)OCCO3]

or a pharmaceutically acceptable complex thereof.

6. The compound of claim 1, represented by the formula:

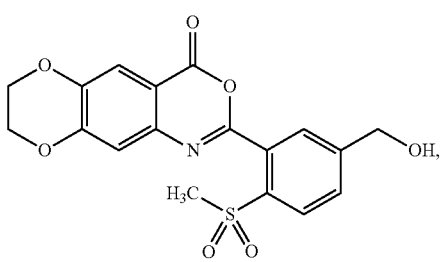 [SMILES: CS(=O)(=O)c1ccc(CO)cc1-c1nc2cc3c(cc2c(=O)o1)OCCO3]

or a pharmaceutically acceptable complex thereof.

7. A pharmaceutical composition comprising a compound of claim 1, and a pharmaceutically acceptable carrier.

8. The pharmaceutical composition of claim 7, wherein said compound has the formula:

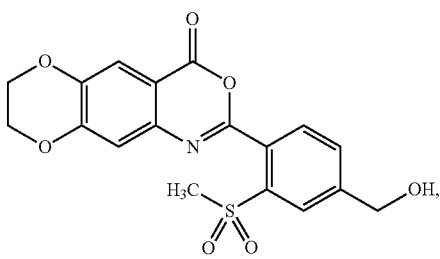

or a pharmaceutically acceptable complex thereof.

9. The pharmaceutical composition of claim 7, wherein said compound has the formula:

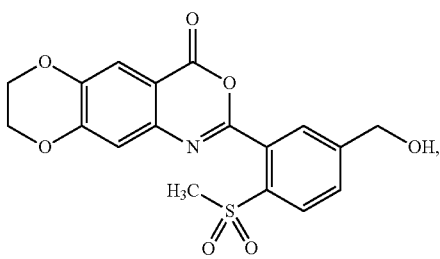

or a pharmaceutically acceptable complex thereof.

10. The pharmaceutical composition of claim 7, prepared for topical administration.

11. A method of treating Netherton Syndrome in a subject in need thereof, comprising administering to said subject an effective amount of a compound having a formula selected from the group consisting of:

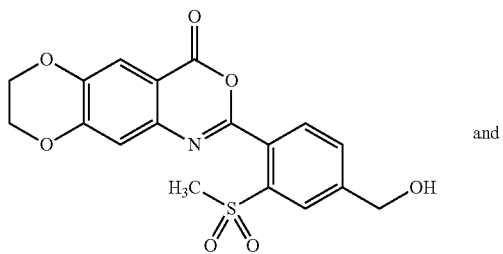

and

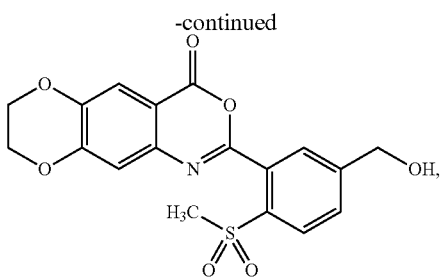

or a pharmaceutically acceptable complex thereof.

12. The method in accordance with claim 11, wherein said compound has the formula:

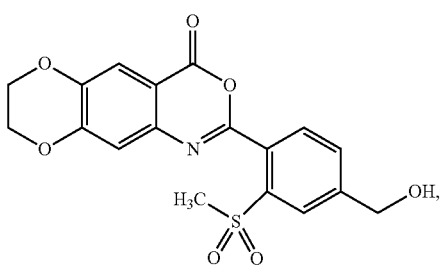 [SMILES: CS(=O)(=O)c1cc(CO)ccc1-c1nc2cc3c(cc2c(=O)o1)OCCO3]

or a pharmaceutically acceptable complex thereof.

13. The method in accordance with claim 11, wherein said compound has the formula:

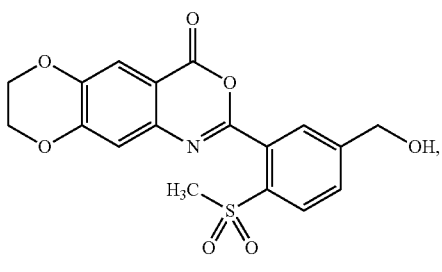 [SMILES: CS(=O)(=O)c1ccc(CO)cc1-c1nc2cc3c(cc2c(=O)o1)OCCO3]

or a pharmaceutically acceptable complex thereof.

14. The method in accordance with claim 11, wherein said compound is administered topically.

* * * * *